US011571467B2

(12) United States Patent
Culp et al.

(10) Patent No.: US 11,571,467 B2
(45) Date of Patent: Feb. 7, 2023

(54) DODECAFLUOROPENTANE EMULSION AS A STROKE AND ISCHEMIA THERAPY

(71) Applicant: The Board of Trustees of the University of Arkansas, Little Rock, AZ (US)

(72) Inventors: William Culp, Little Rock, AR (US); Robert Skinner, Little Rock, AR (US); Evan C. Unger, Tucson, AZ (US)

(73) Assignee: BioVentures, LLC, Little Rock, AR (US)

( * ) Notice: Subject to any disclaimer, the term of this patent is extended or adjusted under 35 U.S.C. 154(b) by 354 days.

(21) Appl. No.: 15/614,570

(22) Filed: Jun. 5, 2017

(65) Prior Publication Data

US 2018/0036389 A1 Feb. 8, 2018

Related U.S. Application Data

(63) Continuation of application No. 14/017,975, filed on Sep. 4, 2013, now abandoned, which is a continuation-in-part of application No. PCT/US2012/027307, filed on Mar. 1, 2012.

(60) Provisional application No. 61/449,448, filed on Mar. 4, 2011.

(51) Int. Cl.
| | |
|---|---|
| *A61K 38/48* | (2006.01) |
| *A61K 38/49* | (2006.01) |
| *A61K 45/06* | (2006.01) |
| *A61K 33/00* | (2006.01) |
| *A61K 31/02* | (2006.01) |

(52) U.S. Cl.
CPC ............ *A61K 38/482* (2013.01); *A61K 31/02* (2013.01); *A61K 33/00* (2013.01); *A61K 38/49* (2013.01); *A61K 45/06* (2013.01)

(58) Field of Classification Search
CPC .............................. A61K 31/02; A61K 38/482
See application file for complete search history.

(56) References Cited

U.S. PATENT DOCUMENTS

| | | | |
|---|---|---|---|
| 6,443,898 B1 * | 9/2002 | Unger ................ | A61K 41/0028 600/458 |
| 2005/0049359 A1 * | 3/2005 | Kei ...................... | A61K 9/0019 524/758 |
| 2010/0055067 A1 * | 3/2010 | Park ...................... | A61K 31/77 424/78.17 |
| 2010/0267842 A1 * | 10/2010 | Kiral ...................... | A61P 17/00 436/124 |

OTHER PUBLICATIONS

Johnson et al., "In Vitro Comparison of Dodecafluoropentane (DDFP), Perfluorodecalin (PFD), and Perfluoroctylbromide (PFOB) in the Facilitation of Oxygen Exchange", Artificial Cells, Blood Substitutes, and Biotechnology, 2009, 37: 156-162. (Year: 2009).*
Bhalla et al., "Management of acute physiological parameters after stroke", QJM: An International Journal of Medicine, vol. 94, Issue 3, Mar. 2001, pp. 167-172. (Year: 2001).*
Culp et al., "Dodecafluoropentane Emulsion Decreases Infarct Volume in a Rabbit Ischemic Stroke Model", J Vasc Interv Radiol. Jan. 2012 ; 23(1): 116-121, published online Nov. 12, 2011., presented, in part, at SIR 2011 Annual Meeting. (Mar. 2011). (Year: 2011).*
Sysoev et al., "Use of ischemic stroke models on rabbits in biomedical research", Pharmacy Formulas, Pharmaceutical Sciences, 2019, vol. 1. No. 1, pp. 10-21. (Russian) (Year: 2019).*
Sysoev et al., "Use of ischemic stroke models on rabbits in biomedical research", Pharmacy Formulas, Pharmaceutical Sciences, 2019, vol. 1. No. 1, pp. 10-21. (machine translation to English) (Year: 2019).*
Culp et al., "Dodecafluoropentane Emulsion in Acute Ischemic Stroke: A Phase Ib/II Randomized and Controlled Dose-Escalation Trial", Journal of Vascular and Interventional Radiology, 2019, vol. 30, Issue 8, pp. 1244-1250. (Year: 2019).*
Australian Application No. 2012225790, Examination Report, dated May 2016.
Australian Application No. 2012225790, Notice of Acceptance, dated Feb. 2017.
Australian Application No. 2017203680, Examination Report, dated Jun. 2018.
Australian Application No. 2017203680, Notice of Acceptance, dated Apr. 2019.
Canadian Application No. 2,829,017, Office Action, dated Jun. 2019.
Chinese Application No. 201280011790.2, Reexamination Decision, dated May 2019.
Chinese Application No. 201280011790.2, Office Action, dated Oct. 2017.
European Application No. 12754641.4, Extended Search Report, dated May 2016.
European Application No. 12754641.4, Intention to Grant, dated Jul. 2019.
Japanese Application No. 2013-556866, Office Action, dated Jul. 2016.
Japanese Application No. 2013-556866, Decision to Grant, dated Oct. 2018.
Korean Application No. 10-2013-7023394, Office Action, dated Aug. 2018.
Korean Application No. 10-2013-7023394, Decision to Grant, dated Apr. 2019.
Korean Application No. 10-2019-7017557, Decision to Grant, dated Aug. 2019.

* cited by examiner

*Primary Examiner* — Laura Schuberg
(74) *Attorney, Agent, or Firm* — Milstein Zhang & Wu LLC

(57) ABSTRACT

The present invention provides methods and combinations for reducing the infarct volume in a tissue of a subject undergoing ischemia or at risk of developing ischemia.

9 Claims, 15 Drawing Sheets

DODECAFLUOROPENTANE EMULSION AS A STROKE AND ISCHEMIA THERAPY

PRIORITY CLAIMS AND RELATED PATENT APPLICATIONS

This application is a continuation of and claims the benefit of priority to U.S. Utility application Ser. No. 14/017,975, filed Sep. 4, 2013, which is a continuation-in-part of and claims the benefit of priority to PCT/US2012/027307, filed Mar. 1, 2012, which is a non-provisional of and claims the benefit of priority to U.S. Provisional Application Ser. No. 61/449,448, filed on Mar. 4, 2011, the entire content of each of which is incorporated herein by reference in its entirety.

GOVERNMENTAL RIGHTS

This invention was made with government support under HL082481 awarded by the National Institutes of Health. The government has certain rights in the invention.

FIELD OF THE INVENTION

The present invention provides methods and combinations for reducing tissue damage in a subject undergoing an ischemic event or at risk of an ischemic event.

BACKGROUND OF THE INVENTION

Situations involving blood loss, ischemia or hypoxia routinely result in organ and tissue damage causing morbidity and mortality. These situations include common surgical and interventional procedures as well as trauma and natural disease states. These episodes present as ischemic syndromes widely distributed throughout the body and extremities and in the brain as strokes. Additionally, clinical procedures including surgery and angiography can produce microemboli resulting in silent or sub-clinical cerebral ischemia as well as clinical strokes. Neuroprotective compounds, hyperbaric oxygen, hemoglobin-based blood substitutes, other approaches, and liquid perfluorocarbon-based oxygen carriers have shown promise but largely failed to compensate in these situations. Prompt revascularization and restoration of oxygenated blood flow remain the primary foci of clinical stroke therapy at this time.

There is a need therefore for another oxygen transport substance that has the ability to physically dissolve, transport, and deliver significant quantities of oxygen and other electron-rich respiratory gases into even the smallest areas of microcirculation and tissues that would not otherwise be oxygenated in an ischemic episode.

SUMMARY OF THE INVENTION

One aspect of the present invention encompasses a method for reducing the infarct volume in a tissue of a subject undergoing ischemia due to an ischemic event. The method comprises administering an effective amount of a composition comprising a perfluorocarbon emulsion to the subject, wherein the infarct volume is reduced without resolving the ischemic event.

Another aspect of the present invention encompasses a method for improving tissue oxygenation in a subject at risk for ischemic tissue damage. The method comprises administering an effective amount of a composition comprising a perfluorocarbon emulsion to the subject prior to a medical procedure that results in the subject being at high risk of ischemic tissue damage.

Yet another aspect of the present invention encompasses a method for improving neuroprotection in a subject at risk for ischemic tissue damage. The method comprises administering an effective amount of a composition comprising a perfluorocarbon emulsion to the subject prior to a medical procedure that results in the subject being at high risk of ischemic neural tissue damage.

Still another aspect of the present invention encompasses a method for treating hemorrhagic stroke. The method comprises administering an effective amount of a composition comprising a perfluorocarbon emulsion to the subject in need of treatment for hemorrhagic stroke.

A further aspect of the present invention encompasses a method for decreasing infarct size due to intracranial brain hemorrhage. The method comprises administering an effective amount of a composition comprising a perfluorocarbon emulsion to the subject in need of treatment for intracranial brain hemorrhage.

An alternative aspect of the present invention encompasses a combination. The combination comprises a composition comprising a perfluorocarbon emulsion and a thrombolytic agent.

Other aspects and iterations of the invention are detailed below.

Figure 9:
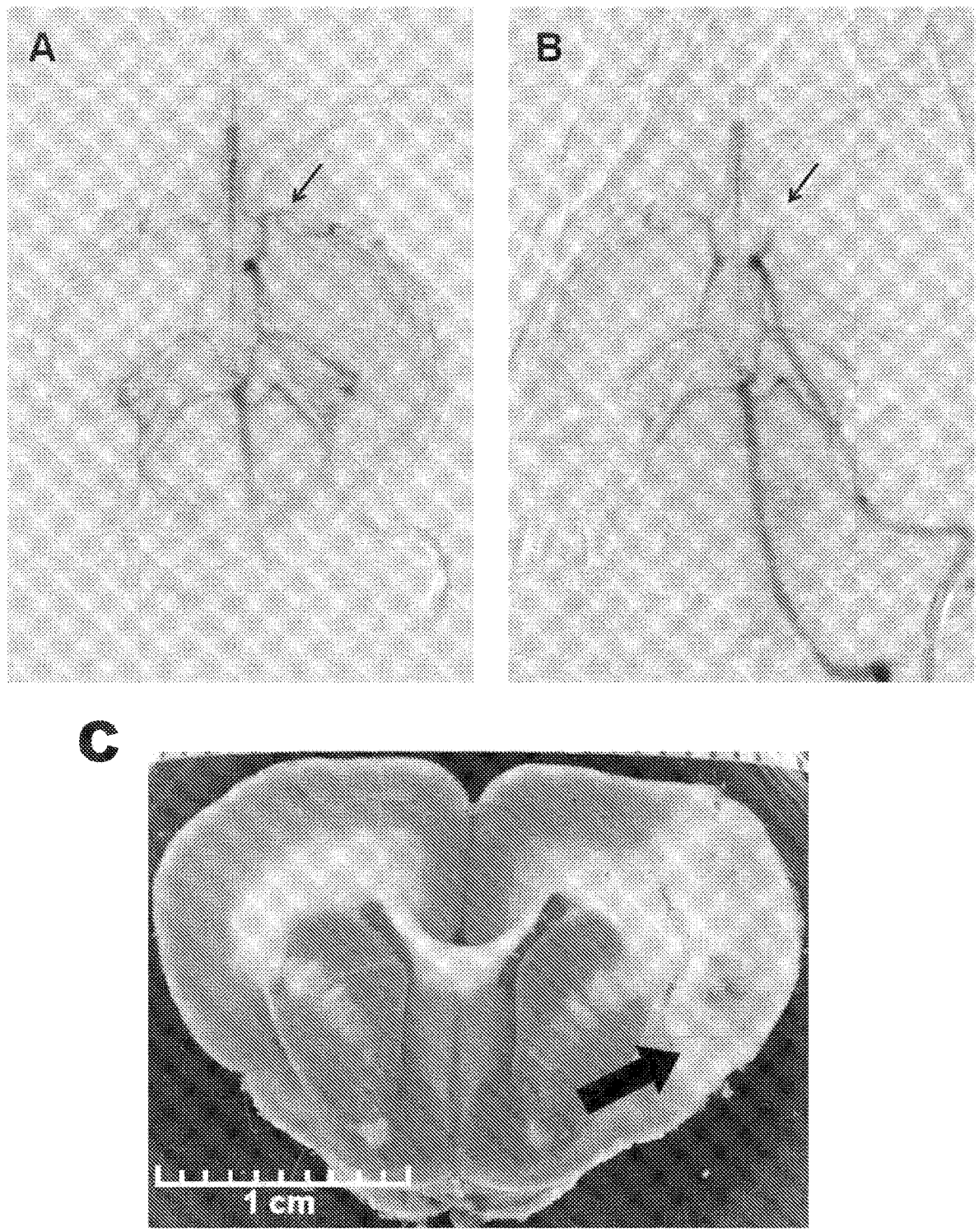

FIG. 9 depicts images of angiographic anatomy (A) embolization of the middle cerebral artery and the anterior cerebral artery (B), and infarct with hemorrhage in a cross section of a rabbit brain (C).

Figure 10:
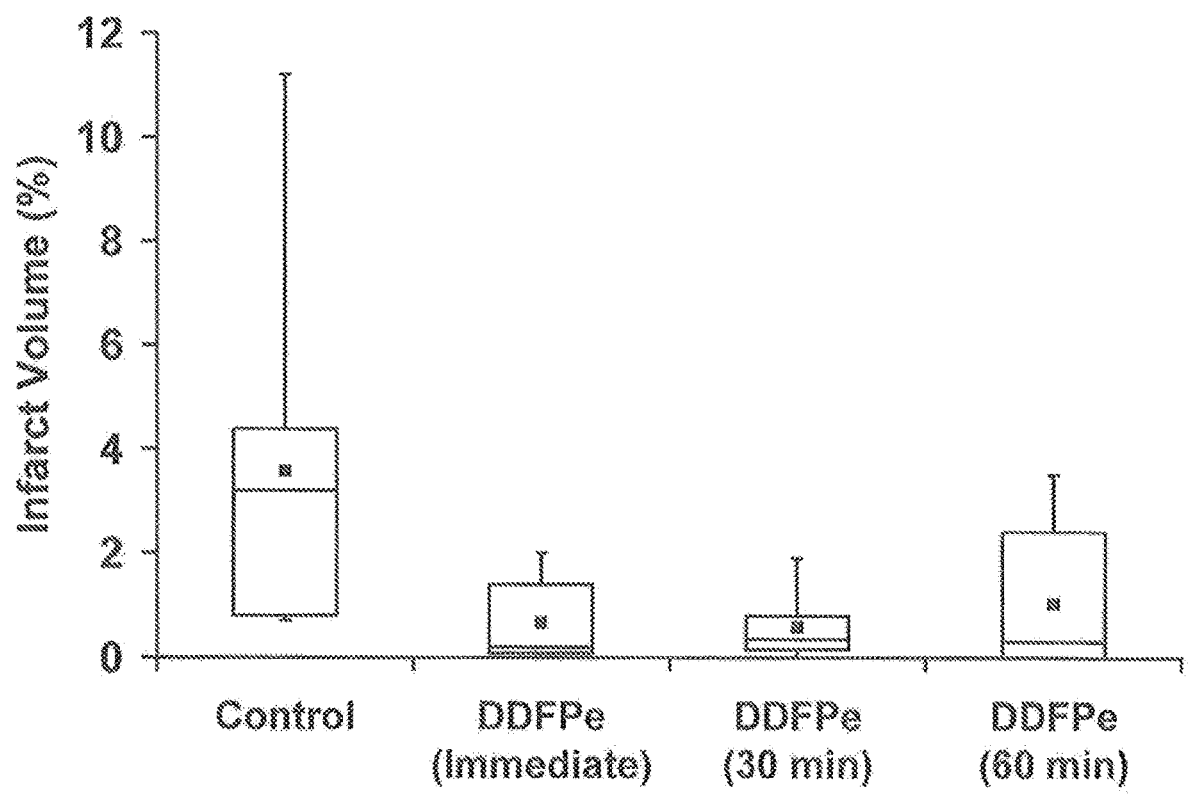

FIG. 10 depicts stroke volumes in ischemic stroke rabbit models receiving DDFPe treatments. DDFPe reduces stroke even when given 60 minutes after permanent arterial occlusion. (Horizontal lines: median, solid squares: mean, vertical lines: maxima and minima, rectangles: $25^{th}$ and $75^{th}$ percentile).

Figure 11:
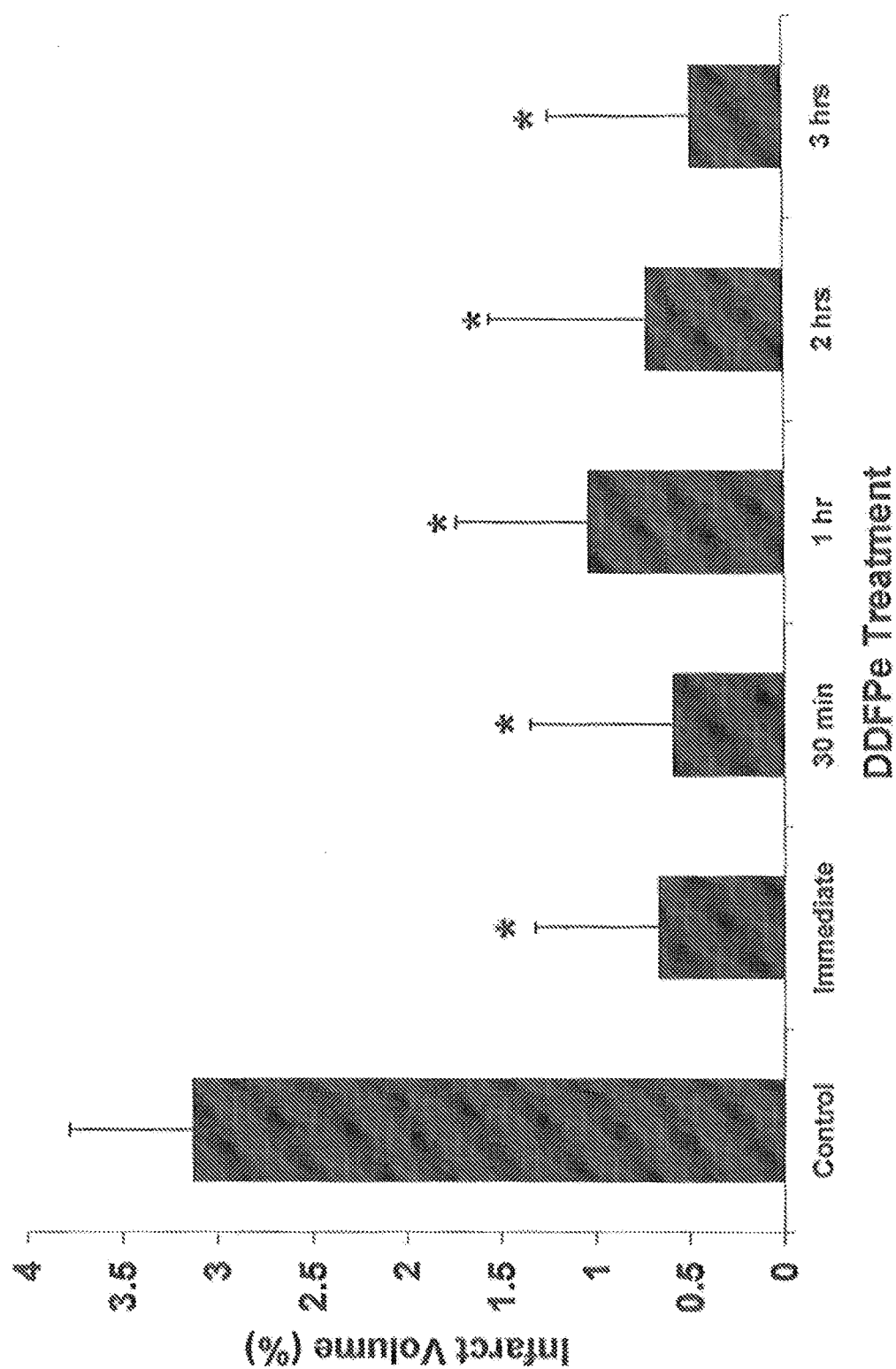

FIG. 11 depicts stroke volumes in ischemic stroke rabbit models receiving DDFPe treatments up to 3 hours after embolization.

Figure 12:
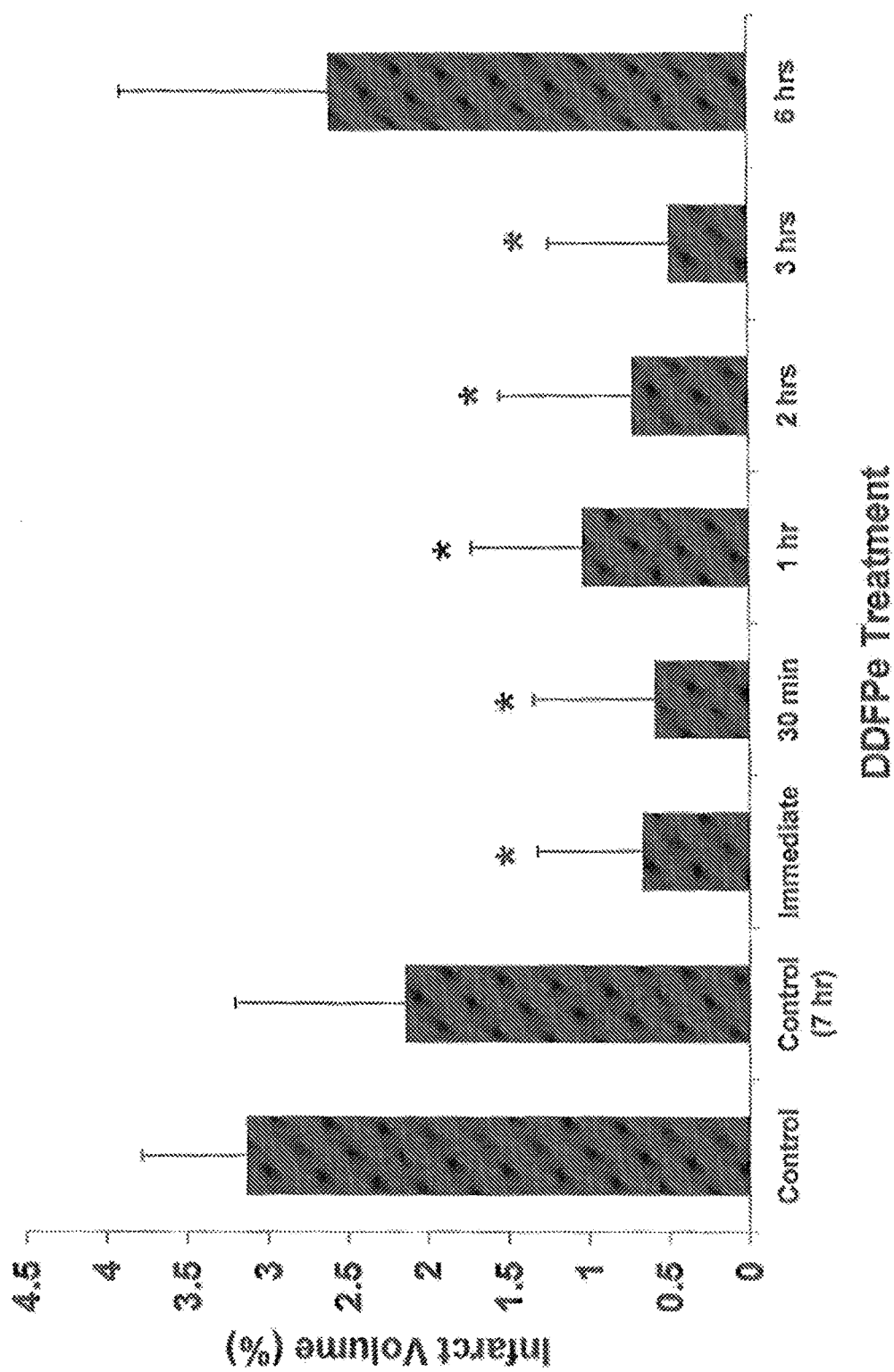

FIG. 12 depicts stroke volumes in ischemic stroke rabbit models receiving DDFPe treatments up to 6 hours after embolization. Note, for FIG. 12, the controls for each time point were as follows:

| Timepoint | Control Value |
| --- | --- |
| 30 min | Control at 4 hrs (leftmost column) |
| 1 hr | Control at 4 hrs (leftmost column) |
| 2 hr | Control at 4 hrs (leftmost column) |
| 3 hr | Control at 4 hrs (leftmost column) |
| 6 hr | Control at 7 hrs |

Figure 13:
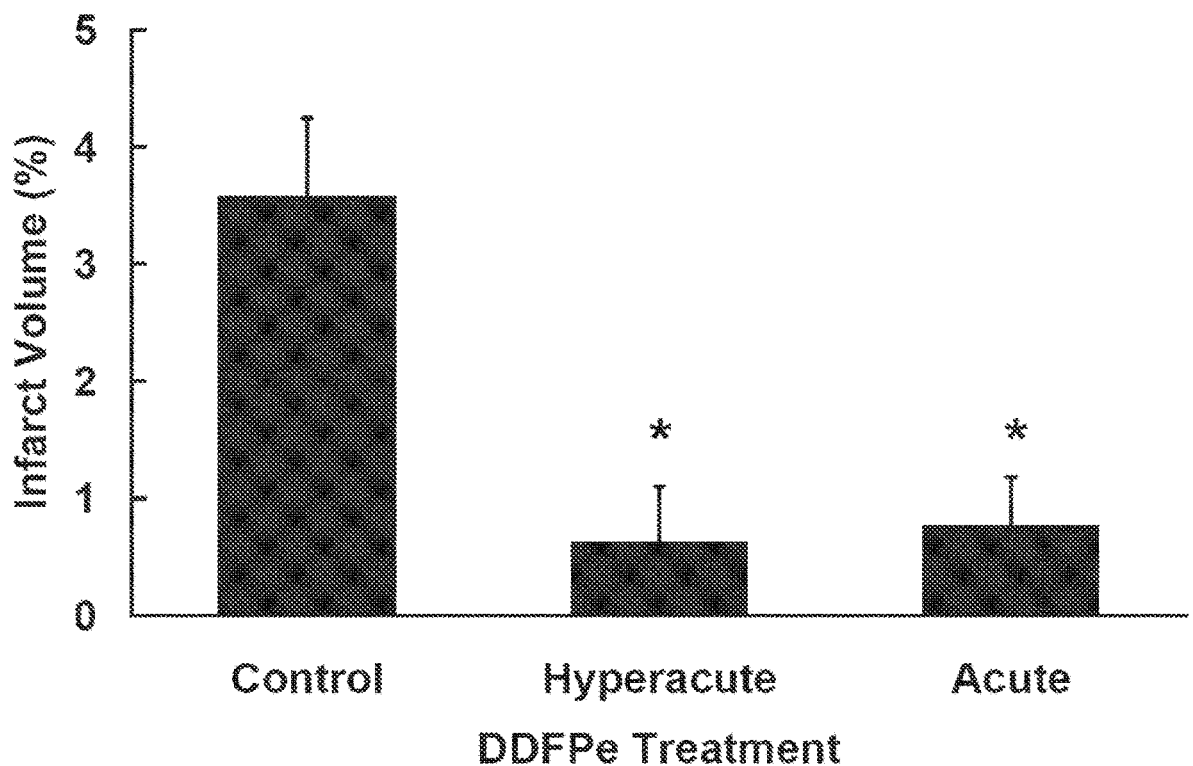

FIG. 13 depicts stroke volumes in ischemic stroke rabbit models receiving DDFPe treatments 0 to 30 minutes after embolization (hyperacute), and 1 to 3 hours after embolization (acute).

Figure 14:
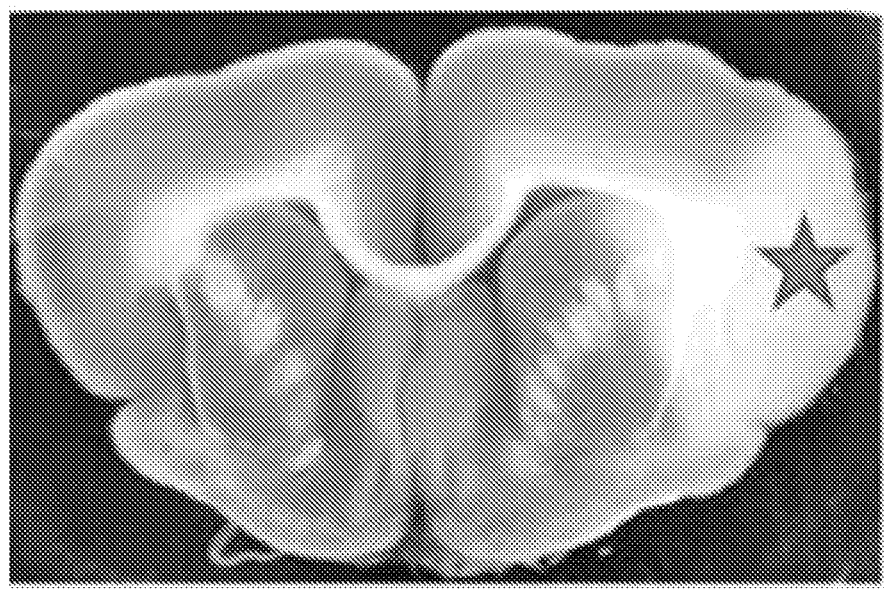
Figure 14:
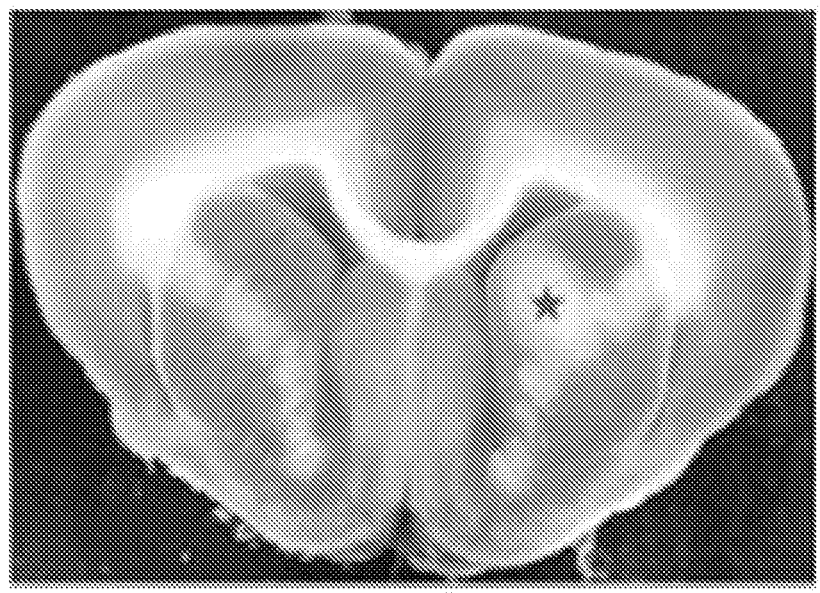

FIG. 14 depicts an image of representative brain sections stained with TTC showing infarct areas. (A) Section from control animal showing the infarct area (large star) of 3.9% (infarct volume as a percent of total brain volume). (B) Section from animal having a stroke and treated with DDFPe showing the infarcted area (small star) of 0.8%.

Figure 15:
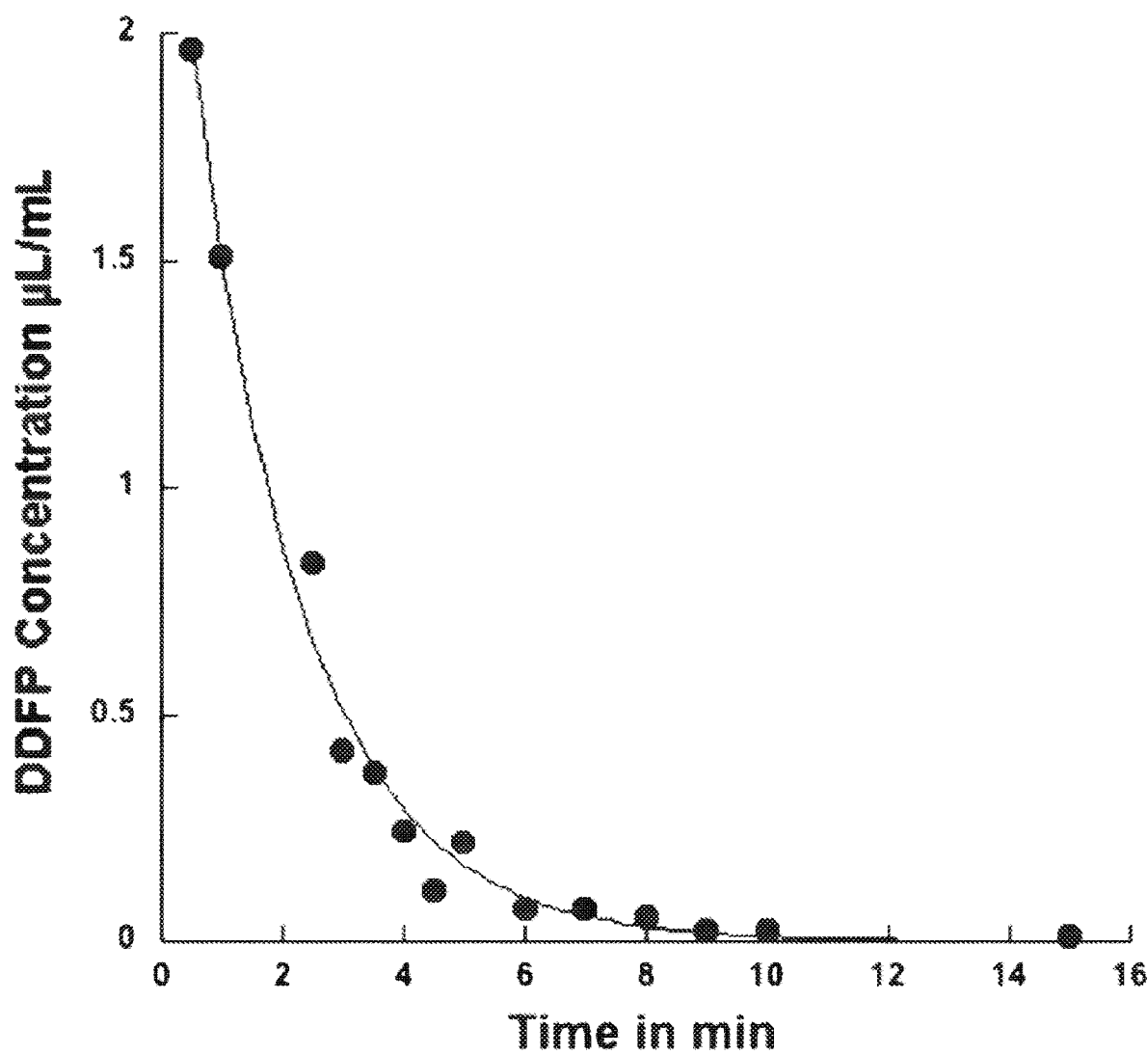

FIG. 15 graphically depicts DDFP clearance from blood as a function of time in a representative rabbit. The DDFPe dose was 0.6 ml/kg of a 2% w/v emulsified preparation. Blood levels of DDFP were determined using a headspace gas chromatograph—mass spectrometer (Varian TSQ). Half-life in blood for this rabbit was 1.68 min. R value was 0.994

DETAILED DESCRIPTION OF THE INVENTION

The present invention describes methods and combinations that may be used to reduce tissue damage due to an ischemic event in a subject. The methods comprise administering a composition or a combination comprising an oxygen transport substance to the subject. In a preferred embodiment, the oxygen transport substance is a composition comprising a perfluorocarbon emulsion. In addition, the methods and combinations are effective in reducing infarct volume and providing neuroprotection to subjects undergoing ischemia, or subjects at risk of ischemia due to a medical procedure. Methods of the invention also encompass reducing tissue damage from hemorraghic stroke or intracranial hemorrhage. Advantageously, the methods and combinations are effective for pretreating subjects at high risk of an ischemic event.

I. Methods of the Invention (a) Method of Reducing Infarct Volume

In one embodiment, the invention encompasses a method for reducing the infarct volume in a tissue of a subject undergoing ischemia due to an ischemic event. The method comprises administering an effective amount of a composition comprising an oxygen transport substance to the subject, wherein the infarct volume is reduced without resolving the ischemic event. In a preferred embodiment, the oxygen transport substance is a composition comprising a perfluorocarbon emulsion.

Generally speaking, the oxygen transport substance may be administered to the subject before the ischemic event is resolved. Stated another way, the oxygen transport substance may be administered to reduce infarct volume even though normal blood flow, blood pressure, or oxygenation levels in the tissue have not been restored.

i. Ischemia

As used herein, the term "ischemia" may refer to a restriction in blood supply, generally due to factors in the blood vessels, with resultant damage or dysfunction of tissue due to inadequate oxygenation. Ischemia may be caused by an "ischemic event." Generally speaking, an "ischemic event" may be caused by an occluded vessel, hypotension, or hypoxia. Non-limiting examples of an ischemic event may include diseases such as sickle cell anemia and Moyamoya disease, or abnormalities in the circulatory system that may lead to occluded vessels or hemorrhage such as volvulus, or hernia, mechanical compression of an artery such as by a tumor, ventricular tachycardia, extremely low blood pressure as a result of heart attack and congenital heart defects, cardio respiratory arrest, hemorrhage, carbon monoxide poisoning, damaging an artery by trauma, or as atherosclerosis or vasculitides, or vasoconstricting an artery such as cocaine vasoconstriction, iatrogenic ischemic episodes such as cardiac surgery or other surgical interventions, coronary and carotid interventions, embolism (foreign bodies in the circulation) such as amniotic fluid embolism, transient clot or bubbles (gaseous emboli), transient ischemic attack (TIA) inflammation, and hypoperfusion episodes, induced g-forces which restrict the blood flow and force the blood to the extremities of the body such as in acrobatics and military flying, localized extreme cold such as by frostbite or improper cold compression therapy, tourniquet application, hypoxia, hypoglycemia (lower than normal level of glucose), arterial and other occlusions such as arterial embolus, thrombus, or atherosclerotic plaque, and stroke. In most of these cases, the disease or abnormality may cause ischemia by forming or increasing the risk of formation of blood clots or hemorrhage which may cause a stoppage of blood supply to a part of the body. In some embodiments, the ischemia may cause stroke.

Ischemia may occur in any organ, tissue or part of the body. For instance, mesenteric ischemia may result from inadequate blood supply to the small intestine; ischemic colitis may result from inadequate blood supply to the large intestine; brain ischemia may result from inadequate blood supply to the brain due to an occluded blood vessel or a hemorrhage leading to hemorrhagic stroke; myocardial ischemia may result from inadequate blood supply to the heart; coronary ischemia may result from inadequate blood supply to the coronary arteries; renal ischemia, also called nephric ischemia, may result from inadequate blood supply to one or both kidneys or nephrons; limb ischemia may result from inadequate blood supply to a limb; anterior ischemic optic neuropathy (AION) may result from inadequate blood supply to the optic nerve.

In certain embodiments, ischemia may be due to a medical procedure. For instance, in some embodiments, ischemia may be due to a medical procedure that increases the risk of vessel occlusion (e.g. medical procedures that produce emboli or microemboli). Non-limiting examples of medical procedures that may increase the risk of vessel occlusion may include major or minor surgical procedure which may cause hemorrhage or the formation of blood clots leading to ischemia, and chiropractic adjustment. Other examples of medical procedures that may cause ischemia include cardiac surgery such as open heart procedures, coronary artery bypass graft surgery, cardiopulmonary bypass surgery, carotid surgery, cardiac surgery, angioplasty, stenting, device implantation, ablations, and heart valve surgery. Still other examples of medical procedures that may cause ischemia include "open surgery" as well as orthopedic surgery, skeletal surgery, and hip fracture fixation surgery.

ii. Infarct

In some embodiments, the invention provides methods for reducing infarct volume in a tissue. In preferred embodiments, the methods of the invention provide for reducing infarct volume in a tissue without increasing incidence of brain hemorrhage. As used herein, the term "infarct" may refer to a lesion caused by tissue damage or death due to ischemia as described in Section I(a)i. above. Methods of measuring infarct volumes are known in the art. For instance, infarct volumes may be measured post-mortem in a tissue or organ by staining the tissue or organ using a live or dead cell stain, followed by measuring the infarcted area in closely spaced sections of the tissue or organ. Alternatively, infarct volume may be measured in a live subject using radiography, computer tomography, magnetic resonance imaging, or other in vivo imaging techniques. Infarct volume may be expressed in volume units, or may be represented as a percentage of the tissue or organ in which it is present.

In some embodiments, infarct volume may be decreased about 100%, 90%, 80%, 70%, 60%, 50%, 40%, 30%, 20%, or 10% compared to an infarct volume when no oxygen transport substance is administered during a comparable ischemic event. For instance, infarct volume may be decreased by about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 6, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10% compared to an infarct volume when no oxygen transport substance is administered during a comparable ischemic event. In an exemplary embodiment, infarct volume may be decreased by about 70 to about 90% compared to an infarct volume when no oxygen transport substance is administered during a comparable ischemic event.

In particular embodiments, infarct volume may be decreased to about 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0 or about 3.1% of the tissue when an oxygen transport substance of the disclosure is administered, compared to an infarct volume of about 3.2% or greater when no oxygen transport substance is administered. In other embodiments, infarct volume may be decreased to about 0, 0.1, 0.2, 0.3, 0.4, 0.5 or about 0.6% of the tissue when an oxygen transport substance of the disclosure is administered, compared to an infarct volume of about 3.2% or greater when no oxygen transport substance is administered. In yet other embodiments, infarct volume may be decreased to about 0.5, 0.6, 0.7, 0.8, 0.9, 1, or about 1.1% of the tissue when an oxygen transport substance of the disclosure is administered, compared to an infarct volume of about 3.2% or greater when no oxygen transport substance is administered. In additional embodiments, infarct volume may be decreased to about 1, 1.1, 1.2, 1.3, 1.4, 1.5, or about 1.6% of the tissue when an oxygen transport substance of the disclosure is administered, compared to an infarct volume of about 3.2% or greater when no oxygen transport substance is administered. In other embodiments, infarct volume may be decreased to about 1.5, 1.6, 1.7, 1.8, 1.9, 2, or about 2.1% of the tissue when an oxygen transport substance of the disclosure is administered, compared to an infarct volume of about 3.2% or greater when no oxygen transport substance is administered. In still other embodiments, infarct volume may be decreased to about 2, 2.1, 2.2, 2.3, 2.4, 2.5, or about 2.6% of the tissue when an oxygen transport substance of the disclosure is administered, compared to an infarct volume of about 3.2% or greater when no oxygen transport substance is administered. In additional embodiments, infarct volume may be decreased to about 2.5, 2.6, 2.7, 2.8, 2.9, 3.0 or about 3.1% of the tissue when an oxygen transport substance of the disclosure is administered, compared to an infarct volume of about 3.2% or greater when no oxygen transport substance is administered. In yet other embodiments, infarct volume may be decreased to about 0, 0.5, 1, 1.5, 2, 2.5, 3.0 or about 3.1% of the tissue when an oxygen transport substance of the disclosure is administered, compared to an infarct volume of about 3.2% or greater when no oxygen transport substance is administered.

(b) Methods for Improving Oxygenation or Providing Neuroprotection Prior to a Medical Procedure Another embodiment of the present invention encompasses a method for improving tissue oxygenation in a subject at risk for ischemic tissue damage. The method comprises administering an effective amount of a composition comprising an oxygen transport substance to the subject prior to a medical procedure that results in the subject being at high risk of ischemic tissue damage. In a preferred embodiment, the oxygen transport substance is a composition comprising a perfluorocarbon emulsion. Non-limiting examples of medical procedures that may result in the risk of ischemic tissue damage are detailed in Section I(a)i above.

Yet another embodiment of the present invention encompasses a method for improving neuroprotection in a subject at risk for ischemic tissue damage. The method comprises administering an effective amount of a composition comprising an oxygen transport substance to the subject prior to a medical procedure that results in the subject being at high risk of neural ischemic tissue damage. In a preferred embodiment, the oxygen transport substance is a composition comprising a perfluorocarbon emulsion. As used herein, the term "neuroprotection" refers to reduced tissue damage in the nervous system of a subject. The nervous system encompasses both the central nervous system and the peripheral nervous system.

(c) Methods for Treating Hemorrhagic Conditions

Still another embodiment of the present invention encompasses a method for treating hemorrhagic stroke. The method comprises administering an effective amount of a composition comprising an oxygen transport substance to the subject in need of treatment for hemorrhagic stroke. In a preferred embodiment, the oxygen transport substance is a composition comprising a perfluorocarbon emulsion.

A further aspect of the present invention encompasses a method for decreasing infarct size due to intracranial brain hemorrhage. The method comprises administering an effective amount of a composition comprising an oxygen transport substance to the subject in need of treatment for intracranial brain hemorrhage. In a preferred embodiment, the oxygen transport substance is a composition comprising a perfluorocarbon emulsion.

(d) Subject

The methods of the present disclosure comprise administering an oxygen transport substance to a subject. Non-limiting examples of a subject in need of an oxygen transport substance may be a rodent, a human, a livestock animal, a companion animal, a laboratory animal, or a zoological animal. In one embodiment, the subject in need of an oxygen transport substance may be a lab animal. Non-limiting examples of a lab animal include a rabbit, a mouse, a guinea pig, a hamster, or a rat. In another embodiment, the subject in need of an oxygen transport substance may be a rodent, e.g. a mouse, a rat, a guinea pig, etc. In yet another embodiment, the subject in need of an oxygen transport substance may be a livestock animal. Non-limiting examples of suitable livestock animals may include pigs, cows, horses, goats, sheep, llamas and alpacas. In another embodiment, the subject in need of an oxygen transport substance may be a companion animal. Non-limiting examples of companion animals may include pets such as dogs, cats, rabbits, and birds. In still yet another embodiment, the subject in need of an oxygen transport substance may be a zoological animal. As used herein, a "zoological animal" refers to an animal that may be found in a zoo. Such animals may include non-human primates, large cats, wolves, and bears. In an exemplary embodiment, the subject in need of an oxygen transport substance may be a human.

In some embodiments, the subject may be undergoing ischemia. In certain embodiments, the subject may be undergoing ischemia caused by an occluded vessel, hypoxia, or hypotension. In an exemplary embodiment, the subject may be undergoing ischemia due to stroke.

In other embodiments, the subject may be at high risk for developing an ischemic event. It will be appreciated by those skilled in the art that a subject may be at high risk for an ischemic event as a result of controllable or uncontrollable risk factors. Non-limiting examples of controllable risk factors may include high blood pressure, atrial fibrillation, high cholesterol, diabetes, atherosclerosis, circulation problems, tobacco use and smoking, alcohol use, physical inactivity, and obesity. Non-limiting examples of uncontrollable risk factors may include age, gender, race, family history, previous stroke or TIA, fibromuscular dysplasia, and patent foramen ovale (PFO or Hole in the Heart).

In yet other embodiments, the subject may be undergoing a medical procedure that increases the risk of an ischemic event. Non-limiting examples of medical procedures that may increase the risk of vessel occlusion may include major or minor surgical or catheter based procedure or interventional which may cause hemorrhage or the formation of blood clots leading to ischemia, and chiropractic adjustment.

In other embodiments, the subject may be in need of treatment for a hemorrhagic stroke.

(e) Preferred Embodiments

In some embodiments, the invention comprises a method for reducing the infarct volume in a tissue of a subject undergoing ischemia caused by an occluded vessel, the method comprising administering an effective amount of a dodecafluoropentane emulsion to the subject, wherein the dodecafluoropentane emulsion improves the oxygenation of the tissue such that the infarct volume is reduced without resolving the occlusion.

In other embodiments, the invention comprises a method for reducing vessel occlusion during a medical procedure that increases the risk for vessel occlusion, the method comprising administering an effective amount of a dodecafluoropentane emulsion to a subject at before the medical procedure is performed. In further embodiments, additional doses of a dodecafluoropentane emulsion may be administered during and/or after the medical procedure is performed.

In yet other embodiments, the invention comprises a method for reducing infarct volume in a tissue of a subject at high risk for developing an occluded blood vessel, the method comprising administering an effective amount of a dodecafluoropentane emulsion to the subject prior to onset of symptoms of an occluded blood vessel.

In each of the above embodiments, the method may further comprise resolving the occlusion.

In other embodiments, the invention comprises a method for treating hemorrhagic stroke, the method comprising administering an effective amount of a dodecafluoropentane emulsion to a subject in need of treatment for a hemorrhagic stroke.

In preferred embodiments, the subject is chosen from a rodent, a research animal, a companion animal, an agricultural animal, and a human.

In other preferred embodiments, the dodecafluoropentane emulsion is administered at least once in a time ranging from immediately after the onset of symptoms of an occluded blood vessel to 24 hours after the onset of symptoms of an occluded blood vessel.

In yet other preferred embodiments, the dodecafluoropentane emulsion is administered to the subject intravenously.

In other preferred embodiments, a solution of about 1% to about 5% w/v of the dodecafluoropentane emulsion is administered to the subject in an amount of about 0.2 mL to about 1 mL per kilogram of the subject.

In yet other preferred embodiments, a solution of about 2% w/v of the dodecafluoropentane emulsion is administered to the subject in an amount of about 0.01 mL per kilogram to about 1 ml per kilogram of the subject.

In other preferred embodiments, the dodecafluoropentane emulsion improves the oxygenation to the tissue such that the infarct volume is reduced without increasing incidence of brain hemorrhage.

In yet other preferred embodiments, the dodecafluoropentane emulsion is administered in combination with an anticoagulant.

In other embodiments, the dodecafluoropentane emulsion is administered in combination with a thrombolytic drug selected from the group consisting of tissue plasminogen activators, antistreptase, streptokinase, urokinase, and combinations thereof.

In yet other embodiments, the dodecafluoropentane emulsion is administered in combination with surgical techniques selected from the group consisting of cardiac surgery, open surgery, orthopedic surgery, and skeletal surgery, angioplasty, stenting, device implantation, and ablations and combinations thereof.

In additional preferred embodiments, the subject is undergoing ischemia due to stroke.

II. Composition

The methods of the present disclosure comprise administering an oxygen transport substance to a subject. In some embodiments, the oxygen transport substance may be blood, a blood product, or a synthetically produced oxygen transport substance. In preferred embodiments, the oxygen transport substance may be a synthetically produced oxygen transport substance. Synthetically produced oxygen transport substances are known in the art and may include hemoglobin-based oxygen carriers and perfluorochemicals. In some embodiments, the synthetically produced oxygen transport substance may be hemoglobin-based oxygen carriers. Non-limiting examples of hemoglobin-based oxygen carriers may be hemoglobin, polymerized hemoglobin, conjugated hemoglobin, crosslinked hemoglobin, phospholipid-encapsulated hemoglobin, recombinant hemoglobin, hemoglobin-based oxygen carriers complexed with superoxide dismutase and catalase, and hemoglobin derivatives. In preferred embodiments, the synthetically produced oxygen transport substance may be perfluorochemicals (PFCs). PFCs may be liquid perfluorochemicals that dissolve oxygen. Non-limiting examples of liquid PFCs that dissolve oxygen and may be used as an oxygen transport substance include perfluorooctyl bromide, perfluorooctyl dibromide, bromofluorocarbons, perfluoroethers, Fluosol DA™, F-44E, 1,2-bisperfluorobutyl-ethylene, F-4-methyl octahydroquinolidizine, 9 to 12 carbon perfluoro amines, perfluorodecalin, perfluoroindane, perfluorotrimethyl bicyclo [3,3,1] onane, perfluoromethyl adamante, and perfluorodimethyl adamantane.

PFCs may also be a gas used to deliver oxygen in the body of a subject. Particularly useful is a PFC gas that has been formulated into microbubbles. Microbubbles comprising PFCs are known in the art and are disclosed in, for example, U.S. Pat. Nos. 5,393,524, 5,409,688, 5,558,854, 5,558,855, 5,595,723, and 5,558,853, all of which are incorporated herein by reference. Non-limiting examples of PFC gases that may be formulated into microbubbles include dodecafluoropentane (DDFPe), sulfur hexafluoride, pentane, hexafluoropropylene, octafluoropropane, hexafluoroethane, octafluoro-2-butyne, hexafluorobuta-1,3-diene, isoprene, octafluorocyclobutane, decafluorobutane, cis-2-pentene, dimethyl sulfide, ethylarsine, bromochlorofluoromethane, trans-2-pentene, 2-chloropropane, hexafluorodisulfide, ethylmercaptan, diethylether, ethylvinylether, valylene, trisfluoroarsine, furfuyl bromide, cis-propenyl chloride, bytyl fluoride, 1,1 dichloroethane, isopropyl methyl ether, isopropylamine, methylfomate, 2-acetyl-furan, ethylenefluoride, 1-pentene, isopropylacetylene, perfluoropentane, isopentane, vinyl ether, 2-butyne, 1,4-pentadiene, tetramethyl silane, dimethyl phosphine, dibromodifluoromethane, 2-chloro-propene, difluroiodomethane, acetaldehyde, trimethyl boric, 3-methyl-2-butene, 1,1 dimethylcyclopropane, aminoethane, vinyl bromide, disilanomethane, trichlorofluoromethane, bromofluoromethane, trifluorodichloromethane, perfluoropentene, and other fluorine containing hydrocarbons. In preferred embodiments, the oxygen transport substance may be microbubbles comprising the PFC dodecafluoropentane (DDFPe).

The preferred fluorocarbons useful as an oxygen therapeutic have a boiling point between about room temperature and at about or near physiological temperature. In one embodiment, the fluorocarbon has a boiling point of below about 100° C. The preferred fluorocarbon is perfluoropentane with perfluoroisopentane being particularly preferred. Other materials include n-perfluoropentane, perfluoropropane (bp −36.7° C.), perfluorobutane (bp=−1.7° C.), perfluorocyclohexane (bp 59-60° C.), perfluoromethylcyclopentane (bp 48° C.), n-perfluorohexane (bp 58-60° C.), perfluorocyclopentane (bp 45° C.) and perfluorotriethylamine (bp 68-69° C.).

For reference, Table A below recites the boiling points of several PFCs.

TABLE A

| PFC | Boiling Point |
|---|---|
| Hexafluoroethane (Perfluoroethane) | −78.2° C. |
| Octafluoropropane (Perfluoropropane) | −36.7° C. |
| Decafluorobutane (Perfluorobutane) | −1.7° C. |
| Dodecafluoropentane (Perfluoropentane) | 29.05-29.45° C. |
| Perfluorohexane (tetradecafluorohexane) | 56° C. |
| Perfluoroheptane (Hexadecafluoroheptane) | 82-84° C. |
| Perfluorooctane (Octadecafluorooctane) | 103-104° C. |

Microbubbles comprising PFCs capable of transporting oxygen in the blood are smaller than red blood cells, and can flow through partially obstructed vessels to deliver large amounts of oxygen to oxygen-starved tissues or organs. Methods of formulating microbubbles comprising PFCs are known in the art, and are disclosed in, for example, U.S. Pat. Nos. 5,393,524, and 5,558,855, each of which are incorporated herein by reference. In essence, microbubbles comprising PFC gas are prepared by a phase-shift technology whereby an emulsion of liquid PFC droplets is prepared in a cool environment, and then when infused or injected into the body of an individual, the droplets become vaporized gas microbubbles comprising a PFC gas.

(a) Emulsion

As used herein, the term "emulsion" may refer to a colloidal dispersion of one immiscible liquid dispersed in another liquid in the form of droplets, whose diameter, in general, exceeds approximately 100 nm and which is typically optically opaque, unless the dispersed and continuous phases are refractive index matched. In general, an emulsion of the invention comprises the dispersed PFC droplets and an amphiphilic material in a continuous phase.

The continuous phase of the colloidal dispersion of the present invention may be an aqueous medium. As used herein, the term "aqueous medium" may refer to a water-containing liquid which may contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. The amphiphilic material may be a biocompatible protein, a fluorine-containing surfactant, polyoxypropylenepolyoxyethylene glycol nonionic block copolymers, and synthetic surfactants.

In some embodiments, the composition of the invention may comprise a surfactant. Non-limiting examples of surfactants that may be used in the composition of the invention may include various commercial anionic, cationic, and non-ionic surfactants, including Tweens, Spans, Tritons, and the like, phospholipids, cholesterol, PLURONIC F-68 ®, HAMPOSYL L30 ® (W.R. Grace Co., Nashua, N.H.), sodium dodecyl sulfate, Aerosol 413 (American Cyanamid Co., Wayne, N.J.), Aerosol 200 (American Cyanamid Co.), LIPOPROTEOL LCO® (Rhodia Inc., Manmmoth, N.J.), STANDAPOL SH 135 ® (Henkel Corp., Teaneck, N.J.), FIZUL 10-127 ® (Finetex Inc., Elmwood Park, N.J.), and CYCLOPOL SBFA 30 ® (Cyclo Chemicals Corp., Miami, Fla.), amphoterics, such as those sold with the trade names: DERIPHAT 170 ® (Henkel Corp.), LONZAINE JS® (Lonza, Inc.), NIRNOL C2N-SF® (Miranol Chemical Co., Inc., Dayton, N.J.), AMPHOTERGE W2 ® (Lonza, Inc.), and AMPHOTERGE 2WAS® (Lonza, Inc.), non-ionic surfactants, such as those with the trade names PLURONIC F-68 ® (BASF Wyandotte, Wyandotte, Mich.), PLURONIC F-127 ® (BASF Wyandotte), BRIJ 35 ® (ICI Americas; Wilmington, Del.), TRITON X-100 ® (Rohm and Haas Co., Philadelphia, Pa.), BRIJ 52 ® (ICI Americas), SPAN 20 ® (ICI Americas), GENEROL 122 ES® (Henkel Corp.), TRITON N42 ® (Rohm and Haas Co.), TRITON N-101 ® (Rohm and Haas Co.), TRITON X-405 ® (Rohm and Haas Co.), TWEEN 80 ® (ICI Americas), TWEEN 85 ® (ICI Americas), BRIJ 56 ® (ICI Americas) and the like, 1,2-dipalmitoyl-sn glycerol-3-phosphoethanolamine-N-4-(p-maleimidophenyl)butyramide, amine-PEG2000-phosphatidylethanolamine, PEG Telomer B, phosphatidylethanolamine, acacia, cholesterol, diethanolamine, glyceryl monostearate, lanolin alcohols, lecithin, including egg-yolk lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan monopalmitate, sorbitan monostearate, stearic acid, trolamine, and emulsifying wax. The above surfactants may be used alone or in combination in the composition of the invention.

Emulsions of fluorocarbons may be prepared, in some embodiments, using fluorosurfactants such as fluorinated phospholipids. For instance, in one embodiment, the surfactant is PEG-Telomer-B. In an exemplary embodiment, the composition comprises DDFPe with PEG-Telomer-B. Phospholipids are also useful for preparing emulsions and may comprise one or more different phospholipids and also fatty acids. Chain length in phospholipids may vary from about 12 to about 20 carbon atoms in length. The alkyl groups may be saturated or unsaturated. Preferably if phospholipids are employed, two or more lipids are employed. For example dipalmitoylphosphatidylcholine can be mixed with dipalmitoylphosphatidylethanolamine-PEG (DPPE-PEG). In this case the pegylated lipid is usually mixed between 1 and 10 mole percent with the non-PEG'ylated lipid. The PEG chain may vary from about 1,000 to 10,000 MW but more preferably is from 2,000 to 5,000 MW. Cholesterol and derivatives of cholesterol such as cholesterol-acetate may be included in the emulsion. The emulsion may contain a cationic (dipalmitoylphosphatidylethylcholine) or anionic lipid (e.g. dipalmitoylphosphatidic acid) or a glycosylated lipid. The lipids or surfactants are mixed with the fluorocarbon and homogenized to prepare an emulsion. One or more viscosity modifying agents may also be included in the emulsion.

The emulsion may also comprise various additives to assist in stabilizing the dispersed phase or in rendering the formulation biocompatible. Acceptable additives include acidifying agents, alkalizing agents, antimicrobial preservatives, antioxidants, buffering agents, chelating agents, suspending and/or viscosity-increasing agents, including triodobenzene derivative, such as iohexol or iopamidol, tonicity agents, acacia, agar, alginic acid, aluminum monostearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

In some embodiments, the oxygen transport substance may be an emulsion of about 0.1% to about 8% w/v dodecafluoropentane. In other embodiments, the oxygen transport substance may be an emulsion of about 0.1% to about 1.5% w/v dodecafluoropentane. In yet other embodiments, the oxygen transport substance may be an emulsion of about 0.5% to about 2.5% w/v dodecafluoropentane. In additional embodiments, the oxygen transport substance may be an emulsion of about 1% to about 3% w/v dodecafluoropentane. In preferred embodiments, the oxygen transport substance may be an emulsion of about 1% to about 5% w/v dodecafluoropentane.

The emulsions may be formed by comminuting a suspension of the dispersed phase in the continuous phase by the application of mechanical, manual, or acoustic energy. Comminuting comprises the process of forming a colloidal dispersion by mixing the liquid dispersed and continuous phases together and then causing a decrease in size of the particles of the dispersed phase from large particles to the size required, using mechanical energy generated by mixing manually, mechanically, or by the action of ultrasound. Appropriate mixing can be achieved in a Microfluidic's Model 110 Microfluidizer apparatus, as described in U.S. Pat. No. 4,533,254, incorporated herein by reference.

Depending on the particular compound, the microbubbles are stabilized to last in the bloodstream for a time ranging from a few minutes to several hours. It will be appreciated by those of skill in the art that the size of the microbubbles formed can be controlled by the manufacturing process to be sufficiently small so as not to obstruct the systemic or pulmonary capillaries and to pass through or around vessels occluded to flow of larger red blood cells. In an exemplary embodiment, the oxygen transport substance may be microbubbles comprising DDFPe, formulated as an emulsion of about 250 nanometer droplets.

(b) Administration

An oxygen transport substance of the disclosure may be administered to a subject by parenteral administration such as via intravenous injection, intra-arterial, intramuscular, intraperitoneal, intraventricular, epidural, intracranial injection, and infusion techniques. In one embodiment, the oxygen transport substance may be administered to a subject by intra-arterial injection. In another embodiment, the oxygen transport substance may be administered to a subject by intramuscular injection. In still another embodiment, the oxygen transport substance may be administered to a subject via intraperitoneal injection. In another embodiment, the oxygen transport substance may be administered to a subject by intraventricular injection. In yet another embodiment, the oxygen transport substance may be administered to a subject by intracranial injection. In another embodiment, the oxygen transport substance may be administered to a subject by epidural injection. In preferred embodiments, the oxygen transport substance may be administered to a subject intravenously.

In some embodiments, the oxygen transport substance may be administered in a bolus. In other embodiments, the oxygen transport substance may be administered continuously. In yet other embodiments, the oxygen transport substance may be administered in a combination of a bolus and continuously. Non-limiting examples of continuous administration may include infusion.

The oxygen transport substance may be administered to a subject once, or multiple times. In some preferred embodiments, the oxygen transport substance may be administered once. In other preferred embodiments, the oxygen transport substance may be administered multiple times. For instance, the oxygen transport substance may be administered 2, 3, 4, 5, 6, 7, 8, 9, 10, 20 or more times. In some embodiments, the oxygen transport substance may be administered 2, 3, 4, 5, 6, 7, 8, 9, or 10 times. In other embodiments, the oxygen transport substance may be administered 9, 10, 11, 12, 13, 14, 15, 16, 17, 18, 19, 20 or more times. In preferred embodiments, the oxygen transport substance may be administered 2, 3, 4, 5, or 6 times.

Yet another preferred method of administration is by sustained IV infusion. When administered by IV infusion an initial bolus or slow IV push loading dose may be administered generally ranging from about 0.01 to about 0.6 cc per kg body weight with 2% w/vol DDFPe. More preferably the loading dose is from about 0.05 to about 0.3 cc per kg. Thereafter the material is infused IV for between about 1 hour and up to 24 hours and even longer depending upon the subject's condition. For sustained infusion the material is generally infused at rates from about 0.01 to about 0.3 cc per kg and more preferably from about 0.025 to about 0.1 cc per kg per hour.

When administered multiple times, the oxygen transport substance may be administered at regular intervals or at intervals that may vary during the treatment of a subject. In some embodiments, the oxygen transport substance may be administered multiple times at intervals that may vary during the treatment of a subject. In preferred embodiments, the oxygen transport substance may be administered multiple times at regular intervals. In some alternatives of the preferred embodiments, the oxygen transport substance may be administered at intervals of about 10, 20, 30, 40, 50, 60, 70, 80, 90, 100, 110, 120, 130, 140, 150, 160, 170, 180, or more minutes. In other alternatives of the preferred embodiments, the oxygen transport substance may be administered at intervals of about 10, 20, 30, 40, 50, 60, 70, 80, 90, 100 or more minutes. In yet other alternatives of the preferred embodiments, the oxygen transport substance may be administered at intervals of about 80, 90, 100 or more minutes. In other alternatives of the preferred embodiments, the oxygen transport substance may be administered at intervals of about 80, 81, 82, 83, 84, 85, 86, 87, 88, 89, 90, 91, 92, 93, 94, 95, 96, 97, 98, 99, 100 or more minutes. In exemplary embodiments, the oxygen transport substance may be administered at intervals of about 90 minutes.

The oxygen transport substance may be administered to a subject undergoing ischemia, prior to development of ischemia, or administered prior to development of ischemia and continued throughout an ischemic episode. For instance, administration of the oxygen transport substance to a subject may be administered prior to development of ischemia when the subject is undergoing a medical procedure that increases the risk of ischemia due to vessel occlusion, or when the subject is at high risk for developing an occluded blood vessel as described in Section 1(b) above. In some embodiments, the oxygen transport substance may be administered to a subject undergoing ischemia. In other embodiments, the oxygen transport substance may be administered to a subject prior to development of ischemia. In yet other embodiments, the oxygen transport substance may be administered to the subject prior to development of ischemia and continued throughout an ischemic episode. In preferred embodiments, the oxygen transport substance may be administered to a subject before a medical procedure that increases the risk of vessel occlusion is performed. In other preferred embodiments, the oxygen transport substance may be administered to a subject at high risk for developing an occluded blood vessel prior to onset of symptoms of an occluded blood vessel.

In some embodiments, the oxygen transport substance may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 minutes or more prior to development of ischemia. In one embodiment, the oxygen transport substance may be administered about 1, 2, 3, 4, 5, 6, 7, 8, 9, 10, 11, 12, 13, 14, 15, 16, 17, 18, 19, 20 minutes prior to development of ischemia. In another embodiment, the oxygen transport substance may be administered about 15, 16, 17, 18, 19, 20, 21, 22, 23, 24, 25, 26, 27, 28, 29, 30 minutes prior to development of ischemia. In yet another embodiment, the oxygen transport substance may be administered about 25, 26, 27, 28, 29, 30, 31, 32, 33, 34, 35, 36, 37, 38, 39, 40 minutes prior to development of ischemia. In another embodiment, the oxygen transport substance may be administered about 35, 36, 37, 38, 39, 40, 41, 42, 43, 44, 45, 46, 47, 48, 49, 50 minutes prior to development of ischemia. In an additional embodiment, the oxygen transport substance may be administered about 45, 46, 47, 48, 49, 50, 51, 52, 53, 54, 55, 56, 57, 58, 59, 60 minutes prior to development of ischemia. In yet another embodiment, the oxygen transport substance may be administered about 55, 56, 57, 58, 59, 60, 61, 62, 63, 64, 65, 66, 67, 68, 69, 70 minutes prior to development of ischemia. In another embodiment, the oxygen transport substance may be administered about 65, 66, 67, 68, 69, 70, 71, 72, 73, 74, 75, 76, 77, 78, 79, 80 minutes prior to development of ischemia. In yet another embodiment, the oxygen transport substance may be administered about 75, 76, 77, 78, 79, 80, 81, 82, 83, 84, 85, 86, 87, 88, 89, 90 minutes prior to development of ischemia. In an additional embodiment, the oxygen transport substance may be administered about 85, 86, 87, 88, 89, 90, 91, 92, 93, 94, 95, 96, 97, 98, 99, 100 minutes prior to development of ischemia. In still another embodiment, the oxygen transport substance may be administered about 95, 96, 97, 98, 99, 100, 101, 102, 103, 104, 105, 106, 107, 108, 109, 110 minutes or more prior to development of ischemia. In a preferred embodiment, the oxygen transport substance may be administered about 25, 26, 27, 28, 29, 30, 31, 32, 33, 34, 35 minutes prior to development of ischemia.

In some embodiments, the oxygen transport substance may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 minutes, or 1, 2, 3, 4, 5, or 6 hours or more after the onset of ischemia. In one embodiment, the oxygen transport substance may be administered about 1, 2, 3, 4, 5, 6, 7, 8, 9, 10, 11, 12, 13, 14, 15, 16, 17, 18, 19, 20 minutes after the onset of ischemia. In another embodiment, the oxygen transport substance may be administered about 15, 16, 17, 18, 19, 20, 21, 22, 23, 24, 25, 26, 27, 28, 29, 30 minutes after the onset of ischemia. In yet another embodiment, the oxygen transport substance may be administered about 25, 26, 27, 28, 29, 30, 31, 32, 33, 34, 35, 36, 37, 38, 39, 40 minutes after the onset of ischemia. In another embodiment, the oxygen transport substance may be administered about 35, 36, 37, 38, 39, 40, 41, 42, 43, 44, 45, 46, 47, 48, 49, 50 minutes after the onset of ischemia. In yet another embodiment, the oxygen transport substance may be administered about 1, 2, 3, 4, 5, or 6 hours or more after the onset of ischemia. In a preferred embodiment, the oxygen transport substance may be administered about 45, 46, 47, 48, 49, 50, 51, 52, 53, 54, 55, 56, 57, 58, 59, 60, 61, 62, 63, 64, or 65 minutes after the onset of ischemia. In another preferred embodiment, the oxygen transport substance may be administered about 1, 2, 3, 4, 5, or 6 hours or more after the onset of ischemia. In an exemplary embodiment, the oxygen transport substance may be administered less than about 1 hour after the onset of ischemia. In another exemplary embodiment, the oxygen transport substance may be administered about 1, 2, or 3 hours after the onset of ischemia.

In some embodiments, the oxygen transport substance may be administered to the subject in an amount of about 0.1, 0.2, 0.3, 0.4, 0.5, 0.6, 0.7, 0.8, 0.9, 1, or about 1.1 mL per kilogram of the subject. In other embodiments, the oxygen transport substance may be administered to the subject in an amount of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or about 0.2 mL per kilogram of the subject. In yet other embodiments, the oxygen transport substance may be administered to the subject in an amount of about 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, or about 0.3 mL per kilogram of the subject. In still other embodiments, the oxygen transport substance may be administered to the subject in an amount of about 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, or about 0.4 mL per kilogram of the subject. In other embodiments, the oxygen transport substance may be administered to the subject in an amount of about 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, or about 0.5 mL per kilogram of the subject. In yet other embodiments, the oxygen transport substance may be administered to the subject in an amount of about 0.41, 0.42, 0.43, 0.44, 0.45, 0.46, 0.47, 0.48, 0.49, 0.5, 0.51, 0.42, 0.53, 0.54, 0.55, 0.56, 0.57, 0.58, 0.59, or about 0.6 mL per kilogram of the subject. In still other embodiments, the oxygen transport substance may be administered to the subject in an amount of about 0.001, 0.005, 0.01, 0.015, 0.02, 0.025, 0.03, 0.035, 0.04, 0.045, 0.05, 0.055, 0.06, 0.065, 0.07, 0.075, 0.08, 0.085, 0.09, or about 0.1 mL per kilogram of the subject. In some preferred embodiments, the oxygen transport substance may be administered to the subject in an amount of about 0.6 mL per kilogram of the subject. In other preferred embodiments, the oxygen transport substance may be administered to the subject in an amount of about 0.3 mL per kilogram of the subject. In yet other preferred embodiments, the oxygen transport substance may be administered to the subject in an amount of about 0.1 mL per kilogram of the subject.

(c) Combination Methods

The oxygen transport substance of the invention may be administered in combination with other treatments for ischemia or treatments that may increase oxygenation of tissue. Non-limiting examples of treatments for ischemia or treatments that may increase oxygenation of tissue may include oxygen inhalation, administration of blood, thrombolytics or anticoagulants, and reducing the temperature of the tissue.

Generally speaking, an administration of an oxygen transport substance of the invention may be used to reduce infarct volume while a secondary treatment is used to resolve the occlusion. Importantly, a composition of the invention may be used to reduce infarct volume during ischemia even though the occlusion is not resolved. Hence, it is envisioned that a composition of the invention is administered to protect tissue, and then treatments to resolve the occlusion may be administered.

In some embodiments, the oxygen transport substance of the invention may be administered in combination with blood. In other embodiments, the oxygen transport substance of the invention may be administered in combination with oxygen inhalation. In yet other embodiments, the oxygen transport substance of the invention may be administered in combination with one or more anticoagulant. Non-limiting examples of anticoagulants may include vitamin K antagonists such as acenocoumarol, coumatetralyl, dicoumarol, ethyl biscoumacetate, phenprocoumon, warfarin, clorindione, diphenadione, phenindione, antiplatelet compounds such as abciximab, eptifibatide, tirofiban, clopidogrel, prasugrel, ticlopidine, cangrelor, elinogrel, ticagrelor, beraprost, prostacyclin, iloprost, treprostinil, acetylsalicylic acid (aspirin), aloxiprin, carbasalate calcium, indobufen, triflusal, dipyridamole, picotamide, terutroban, cilostazol, dipyridamole, triflusal, cloricromen, ditazole, inhibitors of factor Xa such as bemiparin, certoparin, dalteparin, enoxaparin, nadroparin, parnaparin, reviparin, tinzaparin, fondaparinux, idraparinux, danaparoid, sulodexide, dermatan sulfate, apixaban, betrixaban, edoxaban, otamixaban, rivaroxaban, peviparin, YM466, direct thrombin II inhibitors such as bivalirudin, lepirudin, desirudin, argatroban, dabigatran, melagatran, ximelagatran, REG1, defibrotide, ramatroban, antithrombin III, and protein C (Drotrecogin alfa), and thrombolytic drugs such as plasminogen activators (tPA; alteplase, reteplase, tenecteplase), antistreptase, Urokinase, Saruplase, streptokinase, anistreplase, monteplase, ancrod, fibrinolysin, and brinase.

In other embodiments, the oxygen transport substance of the invention may be administered in combination with one or more thrombolytic. Non-limiting examples of thrombolytics may include plasminogen activators (tPA; alteplase, reteplase, tenecteplase), antistreptase, Urokinase, Saruplase, streptokinase, anistreplase, monteplase, ancrod, fibrinolysin, and brinase.

In some preferred embodiments, the oxygen transport substance of the invention may be administered in combination with an anticoagulant or thrombolytic selected from the group consisting of tissue plasminogen activators, antistreptase, streptokinase, urokinase, and combinations thereof. In one alternative of the preferred embodiments, the oxygen transport substance of the invention may be administered in combination with tPA. In exemplary embodiments, tPA may be administered after administration of the oxygen transport substance of the invention, followed by a second dose of the oxygen transport substance as described in the examples.

In other embodiments, a composition of the invention may be combined with lowering the temperature of the tissue suffering the ischemic event. In all instances, however, the tissue temperature is lowered to no less than 29° C. For instance, the tissue temperature may be lowered to about 30, 31, 32, 33, 34, 35, or 36° C.

III. Combination Compositions

In some aspects, the present disclosure provides a combination comprising a dodecafluoropentane emulsion and a thrombolytic. The doedecafluoropentane emulsion and the thrombolytic are as described in Section (I) above. In some embodiments, the combination comprises a thrombolytic selected from the group consisting of tissue plasminogen activators, antistreptase, streptokinase, urokinase, and combinations thereof. In preferred embodiments, the combination comprises a dodecafluoropentane emulsion and tPA. Generally speaking, the effective amount of tPA may be determined using methods commonly known in the art.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

Examples

The following examples illustrate various iterations of the invention.

Example 1. In Vitro Comparison of Dodecafluoropentane (DDFP), Perfluorodecalin (PFD), and Perfluorooctylbromide (PFOB) in the Facilitation of Oxygen Exchange There is a need to develop an intravenous injectable that can increase the exchange of respiratory gases in certain clinical and field situations (e.g. hemorrhagic shock) [1,2]. It is well known that the body needs a constant supply of oxygen as well as an efficient carbon dioxide removal mechanism in order for the cells to maintain healthy metabolic processes. In addition, the extent of benefit from efficient oxygen and carbon dioxide exchange may be dependent upon the time of restoration of this exchange process after a hypoxic event (ischemia reperfusion) [3,4]. The potential applications of a product that can conveniently supplement these needs are widespread, including tumor radiation sensitization [5], elimination of tissue nitrogen in decompression sickness [6], treatment of carbon monoxide poisoning [7], and treatment of various hypoxic conditions that cause cellular damage. Stroke is a serious and widespread condition that can result in neural damage. Such damage is known to be caused in part by a reduction in the opportunity for local brain cells to exchange oxygen and carbon dioxide. Current approved treatments for stroke, such as aspirin, are designed to limit the process of thrombus formation but are not designed to restore tissue viability. Agents such as tissue plasminogen activator (tPA) can currently only be utilized for a 4.5 hour window of time following onset of stroke due to an increased incidence of intra-cranial hemorrhage when administered later [8,9]. It would be interesting and quite beneficial if an agent could be used to extend the window of time for tissue viability so either thrombus dissolving or recanalization life-saving treatment paradigms can be used beyond the current limit. A 2% w/v sub-microemulsion of dodecafluoropentane (DDFP) (also known as perfluoropentane) was developed and has been shown to be safe in humans [10]. This emulsion was proven by Lundgren et al. [11] to carry out respiratory gas transport and maintain tissue viability as well as normal physiological processes in severely anemic rats. Furthermore, Koch et al. [5] have shown that by facilitating the oxygenation of anaerobic tumor cells the formulation can render those cells aerobic, thus making them vulnerable to radiation. The in vitro experiments detailed herein suggest physical characteristics and a gas transport mechanism that indicate how this 2% w/v DDFP emulsion (DDFPe) may function to help maintain tissue oxygen perfusion. The data may also offer insight into how the formulation might be useful as a cellular protectant during stroke or heart attack. When administered in relatively small doses these submicronsized particles (5-10×smaller than red blood cells) may be able to perfuse beyond vascular occlusions, when blood cells are unable, and provide vital oxygen.

Hemoglobin is the sole natural transporter of oxygen in the body. By volume comparison, fluorocarbons are known to dissolve gases more efficiently than other fluids or packed red blood cells [12]. Thus, there are other fluorocarbon emulsions under investigation for gas transport. These other products in development contain relatively large, non-volatile perfluorocarbons (PFCs) such as perfluorodecalin (PFD) and perfluorooctylbromide (P FOB) [13], both having boiling points of 142° C.-144° C. They are formulated in high concentration (20% to 60% w/v) in order to provide adequate oxygen [14-16]. The solubility of oxygen is reported to be 42% and 50% v/v in PFD and PFOB [17,18], respectively. These 2 PFCs also are known to experience a large volume of distribution due to their extreme hydrophobicity. While they are not attracted to lipids, they are strongly repelled by the hydrogen bonding of water, rendering them strongly hydrophobic but only relatively lipophobic. Therefore, they predominantly distribute to the tissues, are notably taken up by the RES macrophages and, due to the high degree of accumulation, they exhibit relatively long secondary phase half-lives [19,20]. This makes their utility as oxygen therapeutics somewhat limited. Alternatively, because the DDFP molecule is smaller, dissolves a higher concentration of oxygen (80% v/v), has a boiling point of 29° C., and thus may volatilize to some degree at biological temperature (further enhancing oxygen load), a much smaller volume of it is needed to supply sufficient oxygen in vivo [6,21,22]. In addition, studies show that DDFP has a 2-minute half-life in the blood and is 99% cleared through the lungs in 2 hours after intravenous administration [23]. Although this short half-life may appear to be a disadvantage, animal studies suggest that a low dose of DDFPe, around 0.7 cc per kg, administered one time as an IV infusion, may be sufficient for resuscitation of severely anemic animals [6,11]. Another consideration is that an oxygen therapeutic does not need to replace blood; it might still have a useful role to stabilize patients with critical anemia or ischemia until additional definitive therapy (e.g. blood transfusion) can be administered. As previously stated, it has been suggested that DDFP has an advantage in solubilizing gases over many other PFCs due to its short linear chain length [1,17] and low boiling point [6,21]. This more efficient oxygen absorption may be attributed to the fact that DDFP has the highest ratio of primary $CF_3$ groups relative to secondary $CF_2$ groups compared to longer chain perfluorocarbons (PFD and P FOB). The $CF_3$ groups, being strongly electronegative, are largely responsible for the attraction of gases [24]. Thus, on a volume basis, liquid DDFP can dissolve more respiratory gases than other linear liquid PFCs. Possibly more important for oxygen-carrying capacity is the fact that DDFP expands from the liquid to the gaseous state [7,25,26] at biological temperatures and as a result transfers gases based on local pressure gradients. It is believed that the gaseous state of DDFP can absorb, deliver, and exchange much more oxygen not only in comparison to its own liquid state but also in comparison to the liquid states of other larger PFCs [21,27]. The goal of this example is to compare the ability of 2% w/v DDFPe with equivalent emulsions of PFD and PFOB for their abilities to pick up oxygen, thus simulating a scenario where oxygen would be available to be carried and delivered to a hypoxic environment. Furthermore, the physical stability of DDFPe is addressed.

Methods

Preparation of the Product

Three separate batches of 2% w/v PFC (DDFP, PFD and PFOB) emulsions were prepared as previously described by Lundgren et al. [6]. In addition, a blank formulation was prepared in the same manner as the 3 emulsions but without any PFC. Specifically, for each 1 liter batch, 3 grams of PEG-Telomer B and 20 grams of PFC (except for the blank) were homogenized along with a 33% sucrose solution using a custom-built semi-closed stainless steel containment system attached to an Avestin Emulsiflex-05 homogenizer. Each homogenate was processed for 6 passes through the chamber at 14,000 psi and then terminally sterile filtered immediately prior to filling into 5 mL vials. The vials were stoppered and crimped and then stored at room temperature.

Product Analysis

Particle Sizing.

Three vials were selected at random from each formulated batch. Vials were vortexed for 5 seconds and 10 µL aliquots of the liquid formulation were removed by syringe, injected into 3 mL cuvettes containing 2 mL of a phosphate buffered saline diluent (of known viscosity), and chilled in an ice bath. The cuvettes were covered and gently inverted 3 times. The temperature of the sample was then measured and each sample was analyzed using a Malvern Zetasizer HS100 at the temperature and viscosity settings determined. The 9 selected vials were each sampled once, unless an error message was given by the Malvern, in which case sampling was repeated until a passing test was achieved. Only the DDFPe particle size was monitored over a 6-month time period.

pH Analysis.

A Symphony SB21 pH meter and a Symphony 850 pH probe were used to determine the pH of the final formulation. Analysis of the hydrogen ion concentration was performed in triplicate. The meter was calibrated with pH standards at 4.0 and 7.0 and then, in order to confirm intra-batch uniformity, 1 vial was selected from the beginning, middle, and end of each batch for measurement.

Statistical Analyses.

All descriptive statistics, such as mean and standard deviation calculations for particle size, pH, oxygen uptake, and volume expansion, were performed using the Microsoft Excel 2003 Data Analysis Kit.

In Vitro Performance Testing

Oxygen Transport.

Figure 1:
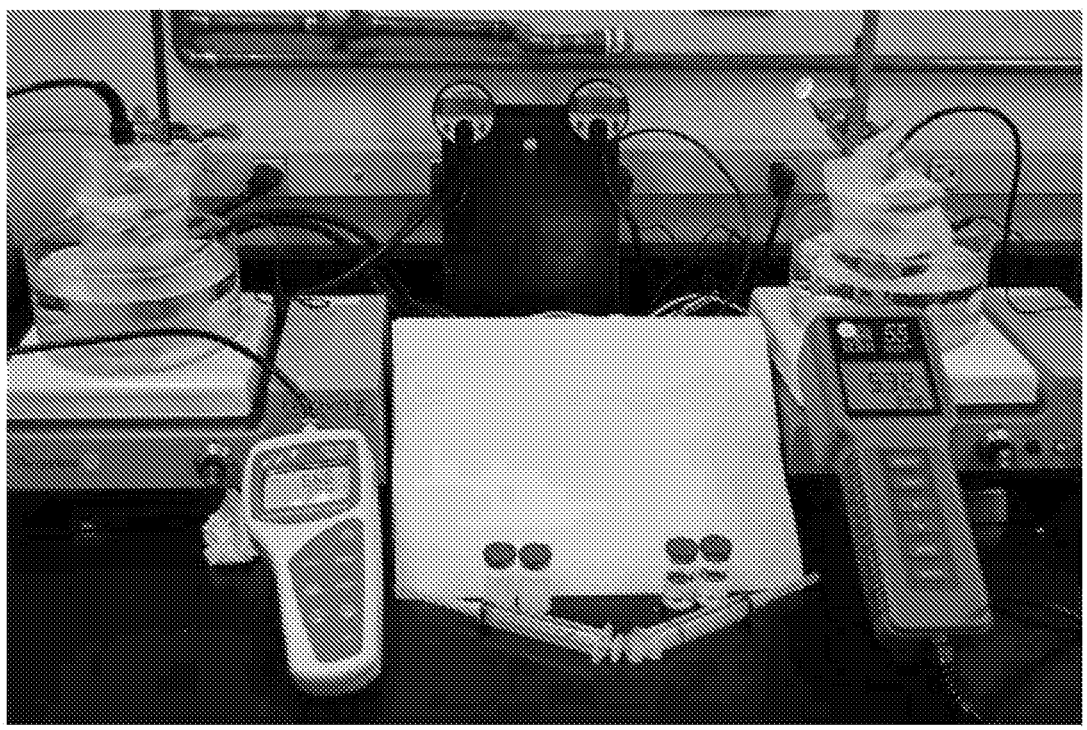
FIG. 1 depicts an image of the set-up used for measuring oxygen absorption. The vials on the left contain one of the PFC emulsions and the vials on the right contain the blank formulation.

The in vitro set-up to measure oxygen uptake by the formulations, shown in FIG. 1, was adapted from Lundgren et al. [11]. Three hundred mL beakers with stir bars were filled with 250 mL of deionized water and placed in temperature-controlled water baths. The water baths were set on top of stirring hotplates. The probes of portable oxygen meters were submerged into the beakers and dissolved oxygen readings were allowed to stabilize. Once stabilization was established, the water surfaces were first covered with Styro-foam® disks and then sealed in Parafilm® to eliminate any headspace and prevent further gas exchange with the atmosphere. A needle and syringe were used to inject 5 mL of formulation through the parafilm and into the 250 mL volume of water (1:50, v:v). The injection hole was resealed each time with adhesive tape. Dissolved oxygen readings were recorded at 30-second intervals on a computer using custom-designed communications port data logger software [28] for 1 hour after each injection. This procedure was carried out in triplicate for the DDFPe, PFDe, PFOBe, and the blank formulation at both temperatures of 20° C. and 37° C.

Volume Expansion.

Figure 2:
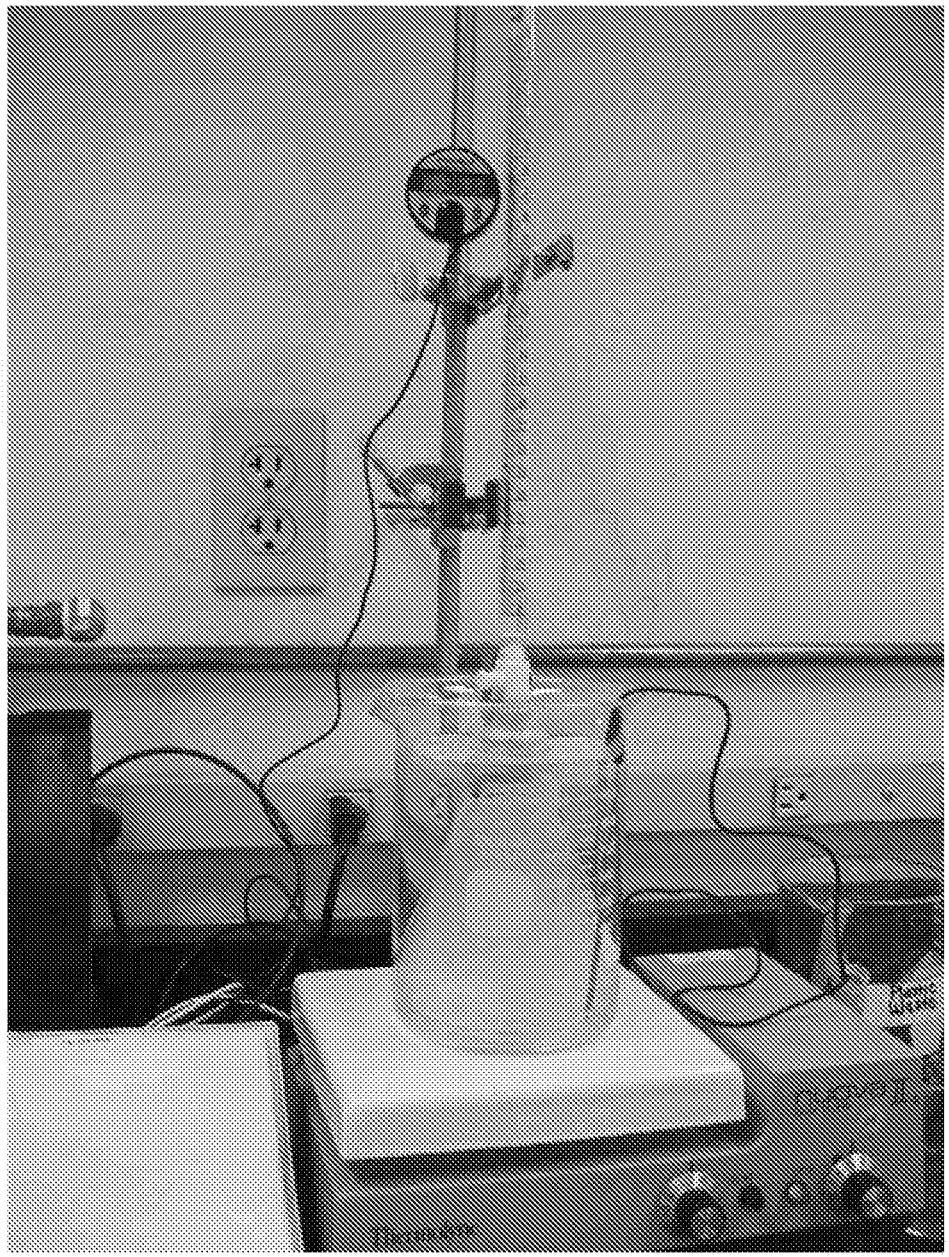
FIG. 2 depicts the set-up used to measure the volume expansion upon injection at 37° C.

Because DDFP is expected to volatilize at 37° C., the volume expansion of each formulation upon injection was tested using a manometer apparatus shown in FIG. 2. In parallel experiments, 5 mL volumes of the DDFPe, PFDe, PFOBe, the blank formulation, and deionized water were injected into 250 mL of stirred DI water while the temperature of the stoppered 250 mL Erlenmeyer flask containing the 250 mL of DI water was maintained at 37° C. A 25 mL burette was inserted through the stopper and its tip submerged into the water such that any volume increase would be forced up into the burette and then could be measured.

Results

Particle Sizing.

Figure 3:
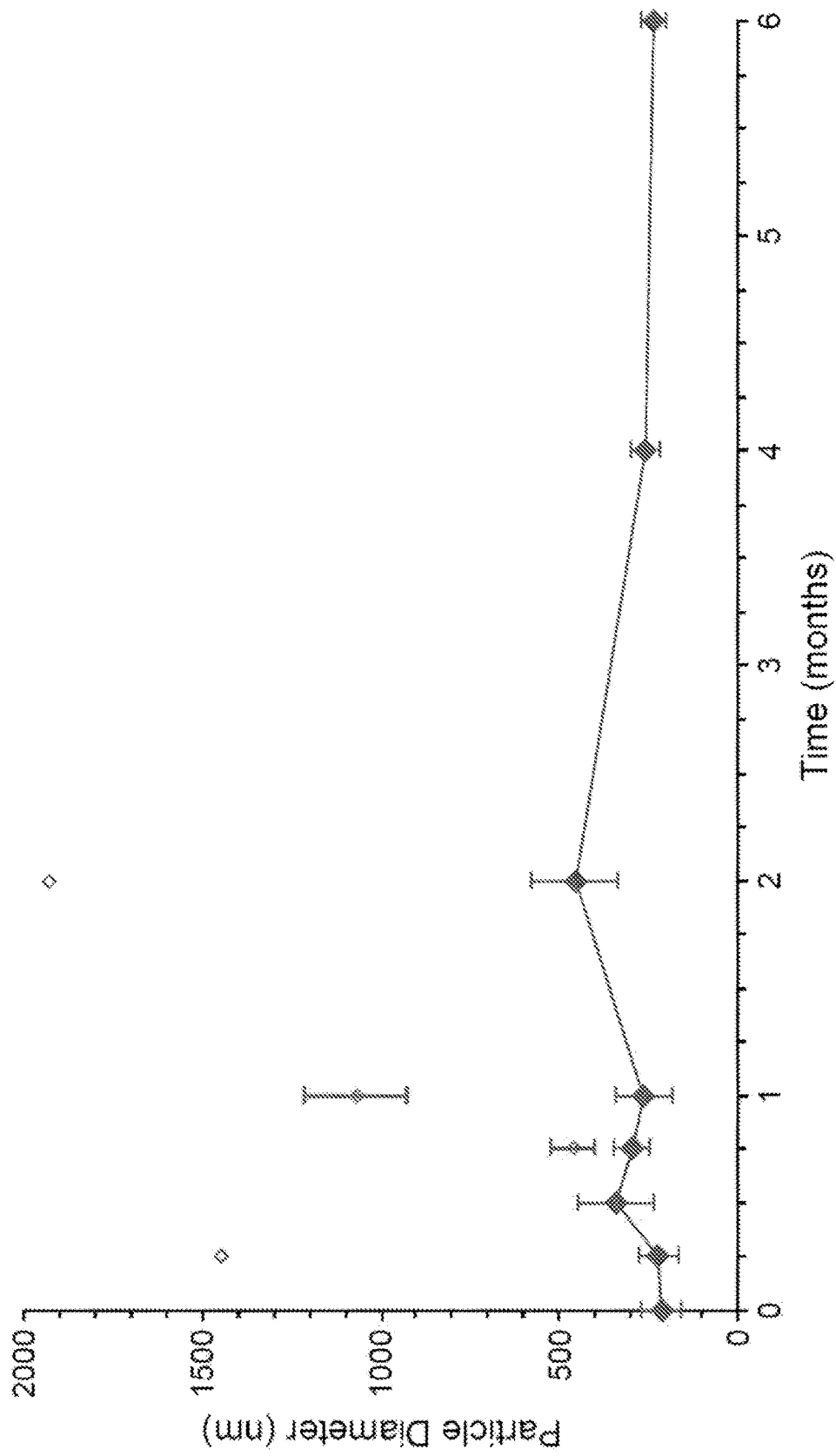
FIG. 3 graphically depicts the particle-size distribution of DDFPe for 6 months at 23° C.±2° C. The error bars represent one standard deviation of the triplicate measurements. The open diamonds represent measurements of less than 2% of the particle distribution at that time point.

The initial average particle diameters were determined to be 215±56 nm, 103±8 nm and 155±6 nm for DDFPe, PFDe and PFOBe, respectively. FIG. 3 shows that the DDFPe particle size remains stable at a diameter below 400 nm for 6 months at room temperature (23° C.±2° C.). Note that the open diamonds represent less than 2% of the particles in the sample and these bimodal distributions were only observed for the first 2 months.

pH Analysis.

The pH values of DDFPe, PFDe and PFOBe were found to be 5.5, 6.1 and 5.7, respectively.

Oxygen Transport.

Figure 4:
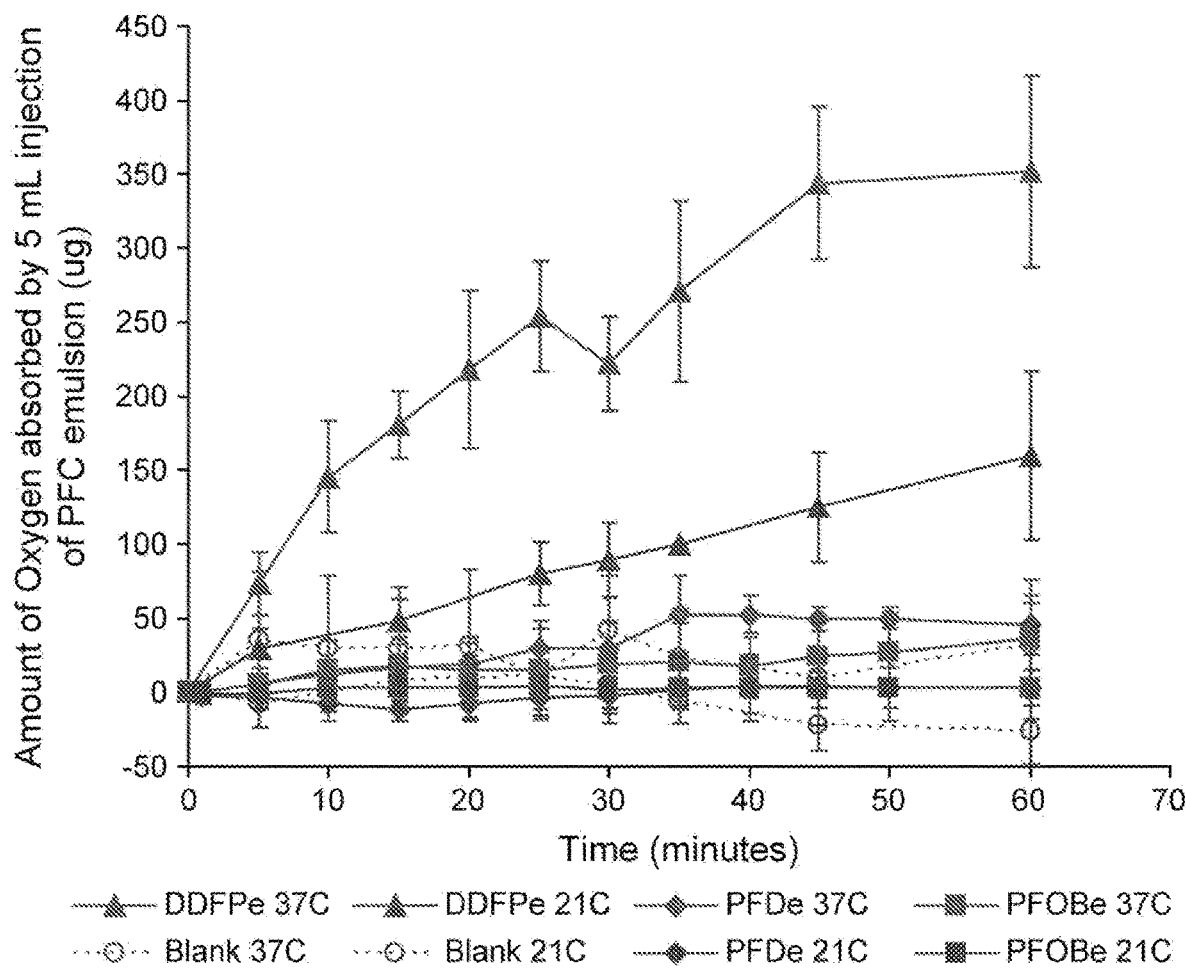
FIG. 4 graphically depicts the amount of oxygen absorbed by 5 mL injections of DDFPe (triangles), PFDe (diamonds), PFOBe (squares), and the formulation blank (open circles) at 21° C. (blue) and 37° C. (red) over the course of 60 minutes.

FIG. 4 shows the oxygen uptake data for all of the samples and controls tested. The PFDe and PFOBe formulations were determined to absorb no more oxygen than the blank formulation at both test temperatures of 21° C. and 37° C. By contrast, DDFPe absorbed significantly more oxygen than the PFDe, the PFOBe, and the blank formulation at both temperatures. Specifically, at 60 minutes, DDFPe absorbed approximately 3 times more oxygen at 21° C. ($p=0.03$) and 7 times more oxygen at 37° C. ($p=0.001$). This can be attributed to two important things. One is the fact that the DDFPe contains approximately twice the molar amount of perfluorocarbon vs. PFC wt amount and the other is the higher ratio of trifluoromethyl groups present per unit volume compared to the other formulations.

Volume Expansion.

Figure 5:
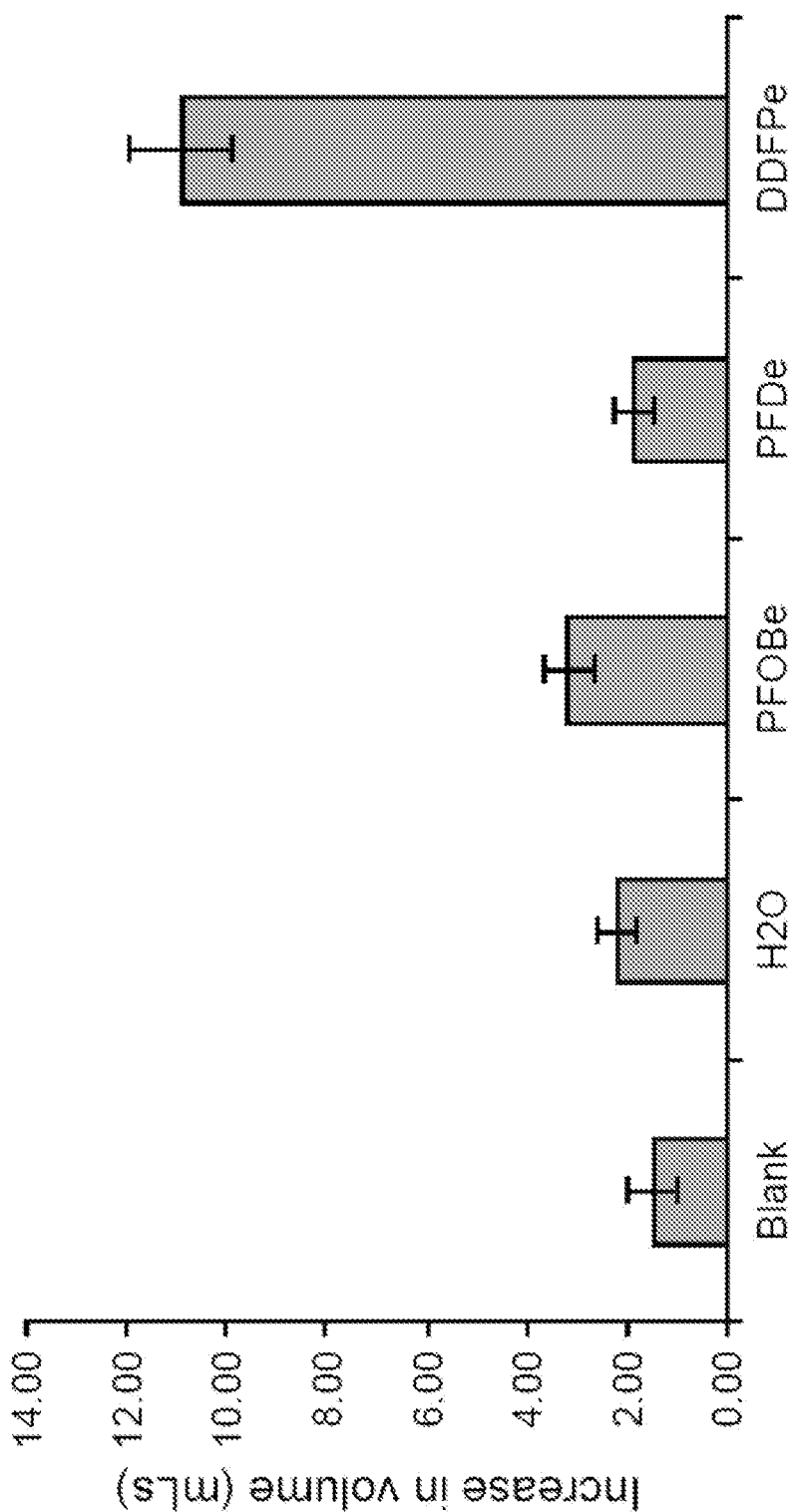
FIG. 5 graphically depicts volume increase upon heating 5 mL injections of the 3 PFC emulsions, the blank formulation, and water to 37° C.

FIG. 5 shows the differences in volume expansion of all the samples and controls when introduced into a 37° C. semi-sealed flask. Although there are expansions observed with PFDe and PFOBe, neither is significantly larger than the expansion of an equal injection of water ($p=0.35$ and $p=0.06$ for PFDe and PFOBe, respectively). There does appear to be a modest difference between the volume increase of PFOBe and the blank formulation ($p=0.01$) but not between water and the blank formulation ($p=0.12$). The reason for the apparent difference between the blank and PFOBe is unknown; however, it is possible that PFOB expands more than PFD at raised temperature. The most notable result is seen in the expansion of the DDFPe. It is significantly greater ($p<0.00001$) than all of the other test injections by at least 5 times.

Conclusion

A 2% w/v DDFP emulsion was prepared and tested against equivalent emulsion concentrations of PFD and PFOB for oxygen absorption ability. The final DDFPe has a pH of 5.5, appears milky white, and the initial particle size is 215±56 nm. The 2% DDFPe was found to carry 7 times more oxygen than 2% w/v emulsions of PFD or P FOB. These differences were determined to be significant at a p=0.001 level of confidence. Thus, the ability of DDFP to expand at physiological temperature appears to provide it with a substantial advantage over PFD and PFOB to deliver a higher payload of oxygen. This is most likely the reason formulations with PFD and PFOB, intended for oxygen delivery, have commonly been prepared at 40% to 60% concentrations. It is clear that DDFP offers a strong advantage over PFD and PFOB in that a much smaller dose of PFC can be administered to achieve the desired result. This is not only less invasive for the patient but also for the environment, as it has been clearly documented that PFCs exit the body through the lungs. The data herein support the contentions of Burkard and Van Liew [21] as well as Lundgren et al. [6,11] in that DDFP should be able to provide enhanced oxygen delivery over other PFCs due to its expansion from a liquid to a gas at physiological temperature. These in vitro studies coupled with the in vivo results obtained by Lundgren et al. [11] in rats appear to indicate that small doses of the DDFP emulsion may also be useful to manage preservation of tissue during acute hypoxic events. Furthermore, results may indicate an additional use for supporting neuroprotection during hypoxic episodes of cardiovascular accidents or stroke.

REFERENCES

1. Dias, A. M. A., Freire, M., Coutinho, J. A. P., Marrucho, I. M. (2004). Solubility of oxygen in liquid perfluorocarbons. Fluid Phase Equilibria. 222-223, 325-330.
2. Cheung, A. T., To, P. L., Chan, D. M., Ramanujam, S., Barbosa, M. A., Chen, P. C., Driessen, B., Jahr, J. S., Gunther, R. A. (2007). Comparison of treatment modalities for hemorrhagic shock. Artif. Cells Blood Substit Immobil. Biotechnol. 35(2):173-190.
3. Schoenberg, M. H., Beger, H. G. (1993). Reperfusion injury after intestinal ischemia. Crit. Care Med. 21(9): 1376-1386.
4. Grace, P. A. (1994). Ischemia-reperfusion injury. Brit. J. Surg. 81:637-647.
5. Koch, C. J., Oprysko, P. R., Shuman, A. L., Jenkins, W. T., Brandt, G., Evans, S. M. (2002). Radiosensitization of hypoxic tumor cells by dodecafluoropentane: a gasphase perfluorochemical emulsion. Cancer Research. 62: 3626-3629.
6. Lundgren, C., Bergoe, G., Olszowka, A., Tyssebotn, I. (2005). Tissue nitrogen elimination in oxygen-breathing pigs is enhanced by fluorocarbon-derived intravascular micro-bubbles. UHM 32(4):215-226.
7. Van Liew, H. D., Burkard, M. E. (1996). Relationship of oxygen content to PO2 for stabilized bubbles in the circulation: theory. J. Appl. Physiol. 81(1):500-508.
8. Fagan, S. C., Morgenstern, L. B., Petitta, A., Ward, R. E., Tilley, B. C., Marler, J. R., Levine, S. R., Broderick, J. P., Kwiatkowski, T. G., Frankel, M., Brott, T. G., Walker, M. D. (1998). The NINDS rt-PA Stroke Study Group. Costeffectiveness of tissue plasminogen activator for acute ischemic stroke. Neurology. 50:883-890.
9. Levi., C. R. (2004). Tissue plasminogen activator (tPA) in acute ischaemic stroke: time for collegiate communication and consensus. The Medical Journal of Australia. 180(12):634-636.
10. Robbin, M. L., Eisenfeld, A. J. (1998). Perflenapent emulsion; a U S contrast agent for diagnostic radiology-multicenter, double-blind comparison with a placebo. Radiology. 207:717-722.
11. Lundgren, C., Bergoe, G., Olszowka, A., Tyssebotn, I. (2006). Intravascular fluorocarbon-stabilized microbubbles protect against fatal anemia in rats. Artificial Cells, Blood Substitutes, and Biotechnology. 34(5): 473-468.
12. Johnson, E. C., Erickson, B. K., Podolsky, A., Birks, E. K., Keipert, P. E., Faithfull, N. S., Wagner, P. D. (1995). Effects of a perfluorocarbon emulsion for enhanced 02 solubility on hemodynamics and 02 transport in dogs. J. Appl. Physiol. 79(5):1777-1786.
13. Lowe, K. C. (2001). Fluorinated blood substitutes and oxygen carriers. Journal of Fluorine Chemistry. 109:59-65.
14. Leese, P. T., Noveck, R. J., Shorr, J. S., Woods, C. M., Flaim, K. E., Keipert, P. E. (2000). Randomized safety studies of intravenous perflubron emulsion. I. Effects on coagulation function in healthy volunteers. Anesth. Analg. 91:804-811.
15. Wahr, J. A., Trouwborst, A., Spence, R. K., Henny, C. P., Ceraianu, A. C., Graziano, G. P., Tremper, K. K., Flaim, K. E., Faithfull, N. S., Clymer, J. J. (1996). A pilot study of the effects of a perflubron emulsion, AF 0104, on mixed venous oxygen tension in anesthetized surgical patients. Anesth. Analg. 82:103-107.
16. Kiral, R. M., Nicora, R., Evitts, D. P. (2002). Comparison of oxygen carrying capacity of a new perfluorocarbon (pfc) blood substitute in rats breathing room air or 100% oxygen. Presented at: APS Intersociety Meeting, San Diego, Calif.
17. Dias, A. M. A., Goncalves, C. M. B., Legido, J. L., Coutinho, J. A. P., Marrucho, I. M. (2005). Solubility of oxygen in substituted perfluorocarbons. Fluid Phase Equilibria. 238:7-12.
18. Krafft, M. P. (2001). Fluorocarbons and fluorinated amphiphiles in drug delivery and biomedical research. Advanced Drug Delivery Reviews 47:209-228.
19. Flaim, S. F. (1994). Pharmacokinetics and side effects of perfluorocarbon-based blood substitutes. Art. Cells, Blood Subst., Immob. Biotech. 22:1043-1054.
20. Tremper, K. K. (1999). Perfluorochemical blood substitutes. Anesthesiology. 91:1185-1187.
21. Burkard, M. E., Van Liew, H. D. (1994). Oxygen transport to tissues by persistent bubbles: theory and simulations. J. Appl. Physiol. 77:2874-2878.
22. Takanori, Y., Schmid-Schönbein, G. W., Cotter, B., De-Maria, A. N. (1999). Flow dynamics of QW7437, a new dodecafluoropentane ultrasound contrast agent, in the microcirculation. J. Amer. Coll. Cardiology 34(2):578-586.
23. Correas, J. M., Meuter, A. R., Singlas, E., Kessler, D. R., Worah, D., Quay, S. C. (2001). Human pharmacokinetics of a perfluorocarbon ultrasound contrast agent evaluated with gas chromatography. Ultrasound in Med. Biol. 27(4): 565-570.
24. Riess, J. G. (2005). Understanding the fundamentals of perfluorocarbons and perfluorocarbon emulsions relevant to in vivo oxygen delivery. Artificial Cells, Blood Substitutes, and Biotechnology 33:47-63.
25. Van Liew, H. D., Burkard, M. E. (1995). Bubbles in circulating blood: stabilization and simulations of cyclic changes of size and content. J. Appl. Physiol. 79 (4): 13791385.
26. Van Liew, H. D., Raychaudhuri, S. (1997). Stabilized bubbles in the body: pressure-radius relationships and the limits to stabilization. J. Appl. Physiol. 82:2045-2053.

27. Van Liew, H. D., Burkard, M. E. (1995). Behavior of bubbles of slowly permeating gas used for ultrasonic imaging contrast. Investigative Radiology 30(5):315-321.
28. Kerschen, A. (2007). Universal COM Logger software (communications port data logger), Tucson, Ariz.
29. Lowe, K. C. (1991). Perfluorochemicals in medicine. Chemistry and Industry 3(83):1-6.
30. Toft, K. G., Hustvedt, S. O., Hals, P. A., Oulie, I., Uran, S., Landmark, K, Normann, P. T., Skotland, T. (2006). Disposition of perfluorobutane in rats after intravenous injection of Sonazoid. Ultrasound in Med. Biol. 32(1): 107-114.

Example 2. Dodecafluoropentane Emulsion Decreases Infarct Volume in a Rabbit Ischemic Stroke Model Many diverse situations involving blood loss, ischemia, or hypoxia result in organ and tissue damage that cause morbidity and mortality. These situations include common surgical and interventional procedures as well as trauma and natural disease states. These episodes commonly present as myocardial infarctions, as other hypoxic or ischemic syndromes widely distributed throughout the body and extremities, and also as ischemic strokes. Additionally, clinical procedures including surgery and angiography can produce microemboli resulting in silent or subclinical cerebral ischemia or actual strokes (1). Neuroprotective compounds, hyperbaric oxygen, hemoglobin-based blood substitutes, other approaches, and liquid perfluorocarbon (PFC)—based oxygen carriers have shown promise but largely failed to compensate in these situations (2-7). Prompt revascularization and restoration of oxygenated blood flow remain the primary foci of clinical stroke therapy at the present time.

Another oxygen transport substance may have therapeutic potential: because of the highly electrophilic fluorine content and lack of intermolecular attractive forces inherent to PFCs, PFC emulsions have the ability to physically dissolve, transport, and deliver significant quantities of oxygen and other electron-rich respiratory gases (8, 9). Sophisticated techniques allow the production of stable PFC emulsions with exceptionally small particles. Such a small-scale droplet allows passage beyond many vascular occlusions that block 8 µm red blood cells, and allows perfusion into even the smallest areas of microcirculation and tissues that would not otherwise be oxygenated by an occluded arterial supply.

Dodecafluoropentane (DDFP) emulsion (DDFPe) is a stable emulsion of 250-nm droplets that, on in vitro administration at 37° C., undergoes expansion into the gaseous state (10 and Example 1). This expansion is unique to DDFP among PFCs. DDFP has a boiling point of approximately 29° C.; thus, at 37° C., large intermolecular "pockets" open up in the DDFPe droplets, such that high concentrations of respiratory gases can be rapidly drawn within. In vitro, the DDFP droplets eventually expand to form microbubbles. However, in vivo, when DDFPe is injected intravenously, it does not expand to true bubble form (Example 1). The intravascular pressure retards full bubble expansion, but fortuitously allows alternation of droplet swelling and contraction as necessary to absorb and release respiratory gases as the droplets travel through the bloodstream without reaching microbubble size. Liquid PFCs do not possess this ability, which renders them relatively limited in their gas-solubilizing abilities. An in vitro comparison of three PFC emulsions demonstrated markedly superior oxygen delivery for DDFPe in the gaseous state (FIG. 4). In vivo, DDFPe functions for approximately 2 hours, and the DDFPe is exhaled through normal respiration without long-term retention in the body (12).

In this example, the intravenous emulsion therapy in a rabbit model of acute ischemic stroke is caused by permanent angiographic occlusions of branches of the internal carotid artery (ICA). The aim is to determine if neuroprotection can be provided without restoration of blood flow.

Materials and Methods

All animal procedures were approved by the institutional animal care and use committee. New Zealand White rabbits (n=95 total) were used in this study. Surgical and angiographic procedures were described previously (13,14). Briefly, rabbits were sedated with intramuscular injection of ketamine 30 mg/kg (Ketaset; Fort Dodge, Fort Dodge, Iowa) and xylazine 3 mg/kg (AnaSed; Lloyd Laboratories, Shenandoah, Iowa) and anesthetized with isoflurane (Novaplus; Hospira, Lake Forest, Ill.). A femoral artery was surgically exposed, and a modified 65-cm angled-tip 3-F catheter (Slip-Cath; Cook, Bloomington, Ind.) was advanced via standard angiographic techniques to select the ICA.

Figure 6:
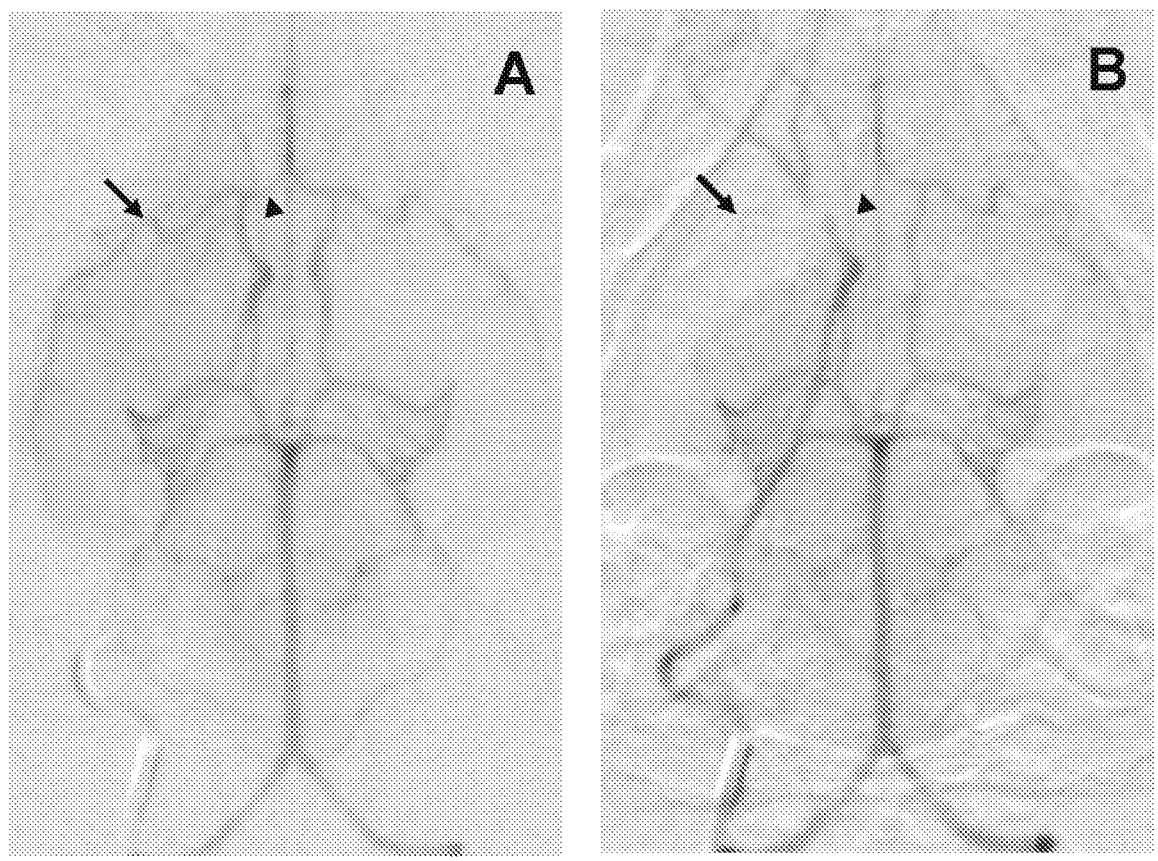
FIG. 6 depicts images of rabbit angiography. Subselective magnification angiograms of the internal carotid artery demonstrate (A) the Circle of Willis and the MCA and ACA (arrow and arrowhead, respectively) and (B) occlusion of the MCA and ACA following the injection of three embolic spheres.

Subselective magnification angiography was performed before embolization and 1 minute after embolization to document the precise occlusion of the cerebral vasculature (FIG. 6). Imaging was performed by using a single-plane C-arm digital mobile imaging system (OEC 9800; GE Healthcare; Salt Lake City, Utah). Embolization with two or three individual microspheres 700-900 µm in diameter (Embosphere; BioSphere, Rockland, Mass.) flushed into the ICA occluded some branches, usually the middle cerebral artery (MCA) and/or anterior cerebral artery (ACA). Repeat angiography 1 minute later confirmed vessel occlusion and compromised flow in the ischemic area. To provide uniform deficits, rabbits with other occlusions or angiographic complications (n=31) were discarded from the study.

Treatments were initiated according to group schedules by using an ear vein catheter access (Instyle-W; Becton Dickinson, Sandy, Utah). Four or 7 hours after embolization, rabbits were euthanized with 1.5 mL of intravenous pentobarbital (Euthasol; Virbac, Fort Worth, Tex.).

For treatments, rabbits were randomly assigned to seven groups in the 4-hour study: (i) control, embolized without therapy (n=7); (ii) pretreatment with DDFPe 30 minutes before embolization (n=7); (iii) immediate DDFPe (n=8); (iv) DDFPe at 30 minutes after stroke (n=5); (v) DDFPe at 1 hour after stroke (n=7); (vi) DDFPe at 2 hours after stroke (n=5); and (vii) DDFPe at 3 hours after stroke (n=6). The administration of therapy was a slow push intravenous dose of DDFPe (2% weight/volume DDFP, 0.6 mL/kg; NuvOx Pharma, Tucson, Ariz.) at the designated group time and repeated every 90 minutes as time before euthanasia allowed.

To observe the limit of treatment efficacy, a parallel study was performed with the use of a much delayed treatment compared with another control group. Groups were control rabbits (n=6), rabbits treated with DDFPe at 1 hour after stroke with additional doses every 90 minutes (n=8), and rabbits treated with DDFPe starting at 6 hours after stroke (n=5). These animals were euthanized 7 hours after embolization.

Figure 7:
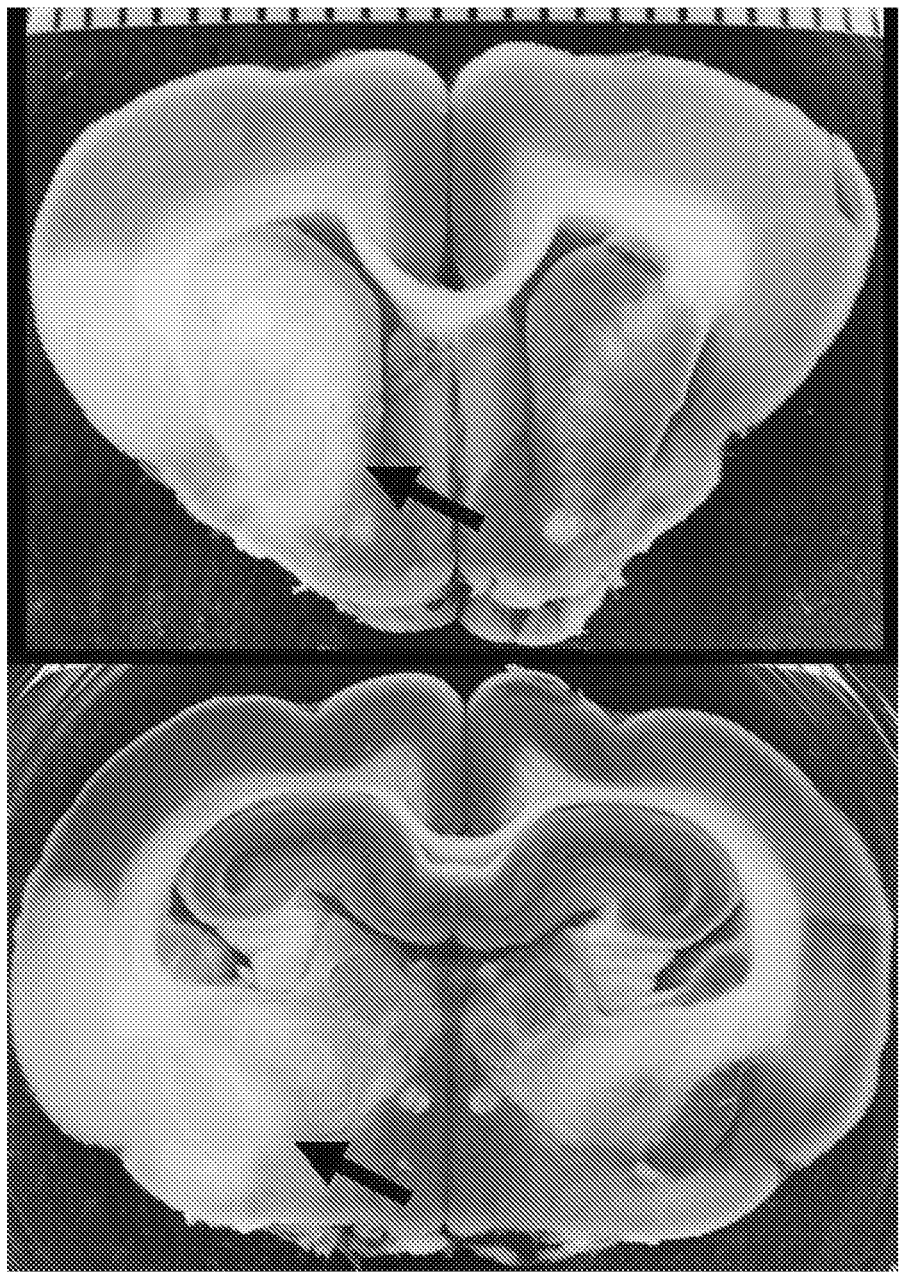
FIG. 7 graphically depicts brain infarction following MCA and ACA embolization. Two sequential sections from a 2,3,5-triphenyltetrazolium chloride (TTC) stained rabbit brain clearly display pale areas of infarct (arrows). The scale bar represents millimeters.

After euthanasia, the brain was harvested, immediately chilled in saline solution, and then sliced coronally at 4.0-mm intervals by using a chilled brain mold (RBM-7000C; ASI Instruments, Warren, Mich.). Brain sections (n=8) were placed in 1% 2,3,5-triphenyltetrazolium chloride (Sigma-Aldrich, St. Louis, Mo.) for 45 minutes at 37° C., fixed in 10% formalin, and digitally photographed (FIG. 7).

Brain size and areas of infarction were measured by using digital analysis (ImageJ software, National Institutes of Health, Bethesda, Md.) by a technician blinded to treatment groups. Infarct volume was calculated as a percentage of the whole brain.

Fixed brain sections were embedded in paraffin and sectioned at 4 μm. After a standard hematoxylin and eosin stain, sections were analyzed and then scored for intracranial hemorrhage (ICH), defined as extravasations of erythrocytes and fluid into the extracellular space (15). The presence and location of ICH were recorded by a veterinary pathologist blinded to treatment groups.

Treatment with DDFPe was combined into three important groups for analysis: pretreatment 30 minutes before embolization, hyperacute treatment less than 1 hour after symptom onset, and acute therapy 1-3 hours after onset.

Because infarct volumes were not normally distributed, ranks of infarct volume percentages were analyzed with the PROC GLM (ie, Kruskal-Wallis equivalent) function of SAS software (SAS, Cary, N.C.). Dunnett-adjusted P values were used in comparing each DDFPe group versus controls. Comparisons of 4- and 7-hour control groups, and of treatment groups within the acute and hyperacute treatment subgroups, were made by using the "exact" procedures in the software package StatXact (Cytel, Cambridge, Mass.). The incidence of hemorrhage within or outside the stroke area was compared by using the $\chi^2$ test and Fisher exact test.

Results

Ninety-five rabbits underwent the angiographic procedure; 11 resulted in severe vasospasm of the ICA and 84 rabbits had successful embolization with permanent occlusion of the MCA and/or ACA. Twenty of these also had occlusion of posterior cerebral or superior cerebellar arteries and were discarded from the study, leaving 64 for analysis. All rabbits were successfully maintained at a normal physiologic state of oxygenation and cardiac function throughout the procedure and treatments.

Figure 8:
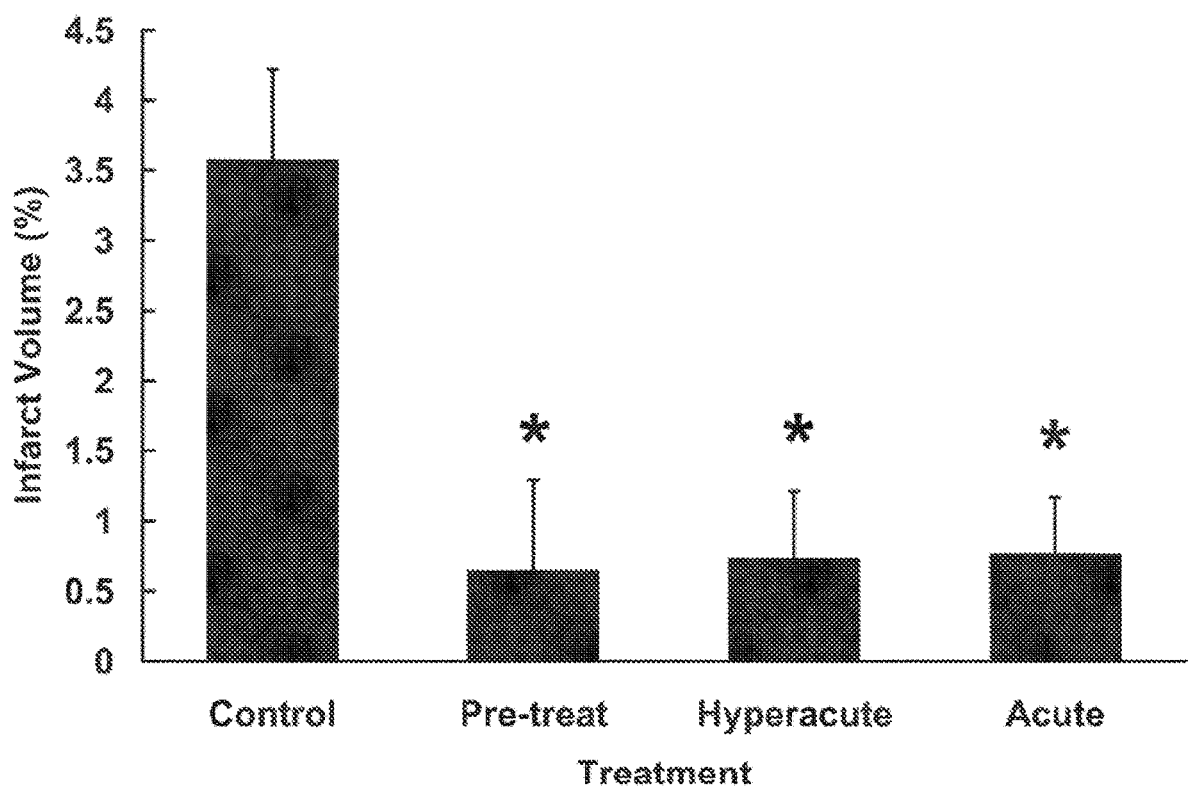
FIG. 8 graphically depicts infarct volume at 4 hours vs. DDFPe treatment time. Categorization of treatment times to model various clinical scenarios, pre-treatment, hyperacute, and acute therapy, demonstrates improved outcomes compared to control. Whether DDFPe is used as a pre-treatment (30 minutes before embolization), a hyperacute treatment (0 to 30 minutes), or an acute treatment (1 to 3 hours), stroke volumes are significantly reduced. *P≤0.021, Dunnett-adjusted comparison of ranks.

In the 4-hour study (Table 1), median infarct volumes were decreased (P=0.001, exact Mann-Whitney test) for all rabbits treated with DDFPe (n=38) compared with controls (0.30% vs 3.20%). The hyperacute group median (n=13; FIG. 8) was significantly reduced (0.30%) compared with controls (P=0.021, Dunnett-adjusted comparison of ranks; unadjusted P=0.008). The acute group median (n=18) was also reduced (0.30%; P=0.005, Dunnett-adjusted comparison of ranks; unadjusted P=0.002). The individual groups within the hyperacute and acute categories did not differ from each other (P=0.54 and P=0.92, respectively, exact Kruskal-Wallis test).

TABLE 1

Influence of DDFPe treatment start time on percent infarct volume at 4 hours. Pre-treat represents DDFPe administration starting 30 minutes before embolization. P-values compare each treatment time to untreated controls

| DDFPe treatment start time | N | Mean ± Standard Error, % | Median, % | P-value (unadjusted) | P-value (Dunnett-adjusted) |
|---|---|---|---|---|---|
| Control | 7 | 3.57 ± 1.41 | 3.20 | — | — |
| Pre-treat | 7 | 0.64 ± 0.37 | 0.30 | 0.008 | 0.04 |
| Immediate | 8 | 0.5 ± 0.35 | 0.20 | 0.010 | 0.05 |
| 30-min | 5 | 0.70 ± 0.32 | 0.40 | 0.083 | 0.32 |
| 1-hour | 7 | 1.03 ± 0.59 | 0.30 | 0.012 | 0.06 |
| 2-hours | 5 | 0.72 ± 0.50 | 0.40 | 0.028 | 0.12 |
| 3-hours | 6 | 0.48 ± 0.28 | 0.25 | 0.008 | 0.04 |

In the 7-hour study (Table 2), control infarct volumes were similar to the 4-hour controls, with a mean of 3.88% and a median of 2.2% (P=0.70, exact Mann-Whitney test). The hour-1 therapy animals had seven of eight values at or below the lowest control value, and the hour-6 therapy animals had three of five at or below the lowest control value.

TABLE 2

Influence of DDFPe treatment start time on percent infarct volume at 7 hours. P-values compare each treatment start time to untreated controls

| DDFPe treatment start time | N | Mean ± Standard Error, % | Median, % | P-value (unadjusted) | P-value (Dunnett-adjusted) |
|---|---|---|---|---|---|
| Control | 6 | 3.88 ± 1.41 | 2.20 | — | — |
| 1-hour | 8 | 1.02 ± 0.69 | 0.25 | 0.007 | 0.01 |
| 6-hours | 5 | 3.92 ± 2.21 | 1.40 | 0.49 | 0.71 |

Microscopic hemorrhage rates were similar in all groups (n=44) in the 4-hour study, both in the stroke area (P=0.85) and outside the stroke area (P=0.32). Hemorrhage within the stroke was seen in 14% of control animals (n=1 of 7), 14% of the DDFPe pretreatment group (n=1 of 7), 14% of the immediate DDFPe group (n=1 of 7), 20% of the 30-min DDFPe group (n=1 of 5), none of the 1-hour DDFPe group (n=7), 20% of the 2-hour DDFPe group (n=1 of 5), and none of the 3-hour DDFPe group (n=6). The incidences of hemorrhage outside of stroke in these groups were 14%, 57%, 28%, 0%, 14%, 20%, and 17%, respectively.

The control rabbits at 7 hours had a numerically greater overall hemorrhage rate compared with 4-hour control animals, but not to a significant level (83% vs 29%; P=0.10). The incidence of hemorrhage within stroke trended downward with treatment with DDFPe at 1 hour and every 90 minutes until euthanasia at 7 hours (P=0.06) compared with control. Hemorrhage within stroke was seen in 67% of control animals (n=4 of 6), none of the 1-hour DDFPe group (n=6), and 60% of the 6-hour DDFPe group (n=3 of 5). Hemorrhage outside of stroke occurred in these groups in 50%, 20%, and 33%, respectively, and did not differ between groups (P=0.82).

Animals that received one DDFPe dose (n=11), two doses (n=25), three doses (n=7), four doses (n=8), and zero doses (ie, controls; n=13) all survived to scheduled euthanasia without apparent adverse events.

DISCUSSION

The search for a neuroprotectant agent to use in acute stroke has been a high priority for many years. The parallel search for blood substitutes has included hemoglobin substitutes and PFCs in liquid form. Numerous studies of the use of these substances in hypoxia and ischemia have encountered side effects and severe complications, and all the agents studied have failed to translate into successful human therapy. Several oxygen free radical scavengers and other novel techniques have shown great promise in small animal stroke models, usually in mouse or rat. None has yet translated into therapy of human stroke (4). Here, a novel oxygen transport approach in an embolic stroke model without the possibility of thrombolysis was tested. This rabbit model of stroke is similar to a model used in the successful development of tissue plasminogen activator (TPA) stroke therapy (16). Although this model is more expensive than rats and mice, its advantage in scale may be important, and it must be noted that other success has translated into human results. This included prediction of the failure of the antioxidant NXY-059 in the Stroke Acute Ischemic NXY-059 Trial (17,18).

Blood has a limited capacity to deliver oxygen, in large part requiring red blood cells to transit capillaries. With decreased blood flow or occlusion, this limitation becomes critical, causing infarction with nearly immediate cell death in some areas and ischemic damage without immediate cell death in others. This threatened area is the penumbra. In many strokes, an ischemic penumbra of potentially viable brain tissue might be saved if oxygen could be delivered there.

Previous therapies including liquid PFC-based oxygen carriers have largely failed to compensate for oxygen deficits. However, DDFPe as a gas at body temperature transports many times more oxygen per weight volume than liquid PFCs (FIG. 4). The intravenous dose of DDFPe is less than 1% of that of other PFC-based agents. The nanosized droplets and bubbles pass—like TPA—through spaces smaller than red blood cells and transport oxygen to ischemic areas blocked from whole blood flow. Other PFC agents require larger doses and are retained within the body on a long-term basis. In human pharmacokinetic studies, intravenous DDFPe as a single smaller dose is well tolerated, and is rapidly cleared by exhalation without significant residual or side effects (12). In rats and pigs, larger doses act for as long as 2 hours (19).

When given intravenously, DDFPe may "pause the clock" on the treatment window for several hours, acting as a bridge to further acute stroke therapies, which might be delayed far beyond current therapeutic time windows. The present rabbit study shows clear benefit in decreased stroke volume compared with untreated controls, not only when DDFPe is given before occlusion or in the hyperacute time period (ie, from 0 to 30 min), but also with delays of 1-3 hours. Whereas prestroke administration could model preventive therapy in high-risk procedures and 0-30-minute therapy could model iatrogenic ischemic episodes, the latter groups model the usual stroke therapy, which is more delayed (20). The continued improved outcome at 3 hours in the present study is very promising in clinical terms, as the most common human therapy, intravenous TPA administration, begins to lose efficacy in this time frame, and endovascular recanalization, which can be performed as long as 6 hours after onset, is limited to major medical centers. This 3-hour improvement raises the possibility of DDFPe actually reversing nonlethal damage in addition to halting further damage. The 7-hour model shows that the damage has progressed too far for statistically significant therapeutic benefit with these small sample sizes at 6-hour administration. Importantly, this model shows that administration at 1 hour can be carried successfully to 7 hours with multiple doses, a point beyond most current thrombolysis protocols now in use. Prolonged success may also be possible. However, safety of multiple large doses is unproven in humans and problematic in dogs, in which rapid doses of DDFPe caused pulmonary hypertension and severe symptoms (21).

Measurements of intracranial hemorrhage (ICH) rates 4 hours after stroke were similar in all groups. The trend for increased rates of hemorrhage in control rabbits at 7 hours suggests that this time window of several hours after onset is important in the development of microscopic bleeding. Particularly encouraging is the absence of ICH in the 7-hour group treated with DDFPe from 1 hour (15,22). This raises the possibility of a protective aspect in this therapy, but needs to be confirmed with larger numbers of animal studies (23 and FIG. 9).

In addition to ischemic and hemorrhagic acute strokes, clinical applications might also include pretreatment of high-risk cardiac and carotid surgeries or neurovascular or cardiac interventions, providing a few hours of improved tissue oxygenation during iatrogenic ischemic episodes. Many strokes, cognitive deficits, or myocardial infarctions caused by transient clot, bubbles, or hypoxia might be completely avoided. Gaseous emboli and hypoperfusion episodes associated with surgery and vascular or cardiac interventions are transient phenomena and may require no additional therapy after DDFPe treatment. As human single-dose experience appears safe, this testing could quickly progress.

In addition to the need to fully investigate the time course of effectiveness of DDFPe, another limitation of the present study is the lack of therapeutic dosage testing. These studies used established dose levels for sonographic imaging, and optimization of therapeutic dose levels in rabbits and humans is required. Although considerable benefit was demonstrated at the chosen dosage and time points, further studies that compare other artificial oxygen carriers and fully characterize the treatment effects are needed. Moreover, the use of DDFPe must be examined in a thromboembolic stroke model as a combination treatment with intravenous TPA thrombolysis, intraarterial interventions, or sonothrombolysis with microbubbles and ultrasound (US). Here, safety and synergistic or additive effects will be appraised. If continued preclinical research overcomes these limitations, human feasibility testing in acute stroke can rapidly advance.

Human dosage, timing, efficacy, and safety may be further optimized. This will be facilitated by the previous study of DDFPe as a US contrast agent in more than 2,000 patients and its approval as a US contrast agent by the European Agency for the Evaluation of Medicinal Products (now known as the European Medicines Agency) (24,25). The current single dose is similar to that used as a human contrast agent, and dose optimization for therapeutic uses and safety testing of multiple doses have not yet been performed. Although reports of DDFPe as a contrast agent were very positive, development stopped for economic reasons, and DDFPe is not commercially available at this time.

Intravenous DDFPe protects brain tissue from ischemia, possibly by decreasing the degree of hypoxia. It decreases infarct volumes in stroke, and the effect can be sustained for several hours with repeated doses. Safety in humans has been demonstrated. Further animal studies and rapid development as a therapeutic oxygen delivery agent during times of stroke, blood loss, ischemia, and hypoxia, and in some preventive situations such as high-risk procedures, are warranted.

REFERENCES FOR EXAMPLE 2

1. Jurga J J, Nyman J, Tornvall P, et al. Cerebral microembolism during coronary angiography. Stroke 2011; 42:1475-1477.
2. Kim H W, Greenburg A G. Artificial oxygen carriers as red blood cell substitutes: a selected review and current status. Artif Organs 2004; 28:813-828.
3. Pignataro G, Simon P, Xiong Z G. Prolonged activation of ASIC1a and the time window for neuroprotection in cerebral ischaemia. Brain 2007; 130:151-158.

4. Donnan G A. The 2007 Feinberg Lecture: a new road map for neuroprotection. Stroke 2008; 39:242-248.
5. Fergusson D A, McIntyre L. The future of clinical trials evaluating blood substitutes. JAMA 2008; 299:2324-2326.6. Vinukonda G, Csiszar A, Hu F, et al. Neuroprotection in a rabbit model of intraventricular haemorrhage by cyclooxygenase-2, prostanoid receptor-1 or tumour necrosis factor-alpha inhibition. Brain 2010; 133:2264-2280.
7. Liesz A, Zhou W, Mracskó É, et al. Inhibition of lymphocyte trafficking shields the brain against deleterious neuroinflammation after stroke. Brain 2011; 134:704-720.
8. Reiss J G. Understanding the fundamentals of perfluorocarbons and perfluorocarbon emulsions relevant to in vivo oxygen delivery. Artif Cells Blood Substit Immobil Biotechnol 2005; 33:47-63.
9. Remy B, Deby-Dupont G, Lamy M. Red blood cell substitutes: Fluorocarbon emulsions and haemoglobin solutions. Br Med Bull 1999; 55:277-298.
10. Correas J M, Quay S C. EchoGen emulsion: a new ultrasound contrast agent based on phase shift colloids. Clin Radiol 1996; 51(Suppl 1):11-14.
12. Correas J M, Meuter A R, Singlas E, Kessler D R, Worah D, Quay S C. Human pharmacokinetics of a perfluorocarbon ultrasound contrast agent evaluated with gas chromatography. Ultrasound Med Biol 2001; 27:565-570.
13. Culp B C, Brown A T, Erdem E, Lowery J, Culp W C. Selective intracranial magnification angiography of the rabbit: basic techniques and anatomy. J Vasc Intery Radiol 2007; 18:187-192.
14. Brown A T, Skinner R D, Flores R, et al. Stroke location and brain function in an embolic rabbit stroke model. J Vasc Intery Radiol 2010; 21:903-909.
15. Flores R, Hennings L J, Lowery J D, Brown A T, Culp W C. Microbubble-augmented ultrasound sonothrombolysis decreases intracranial hemorrhage in a rabbit model of acute ischemic stroke. Invest Radiol 2011; 46:419-424.
16. Zivin J A, Fisher M, DeGirolami U, Hemenway C C, Stashak J A. Tissue plasminogen activator reduces neurological damage after cerebral embolism. Science 1985; 230:1289-1292.
17. Lapchak P A, Araujo D M, Song D, Wei J, Zivin J A. Neuroprotective effects of the spin trap agent disodium-[(tert-butylimino)methyl]benzene-1,3-disulfate N-oxide (generic NCY-059) in a rabbit small clot embolic stroke model: combination studies with the thrombolytic tissue plasminogen activator. Stroke 2002; 33:1411-1415.
18. Diener H C, Lees K R, Lyden P, et al. SAINT I and II Investigators. NXY-059 for the treatment of acute stroke: pooled analysis of the SAINT I and II Trials. Stroke 2008; 39:1751-1758.
19. Lundgren CEG, Bergoe G W, Tyssebotn I M. Intravascular fluorocarbonstabilized microbubbles protect against fatal anemia in rats. Artif Cell Blood Substitutes 2006; 34:473-486.
20. McKhann G M, Grega M A, Borowicz L M Jr, Baumgartner W A, Seines O A. Stroke and encephalopathy after cardiac surgery, an update. Stroke 2006; 37:562-571.
21. Grayburn P A, Erickson J M, Escobar J, Womack L, Velasco C E. Peripheral intravenous myocardial contrast echocardiography using a 2% dodecafluoropentane emulsion: identification of myocardial risk area and infarct size in the canine model of ischemia. J Am Coll Cardiol 1995; 26:1340-1347.
22. Brown A T, Flores R, Hamilton E, Roberson P K, Borrelli M J, Culp W C. Microbubbles improve sonothrombolysis in vitro and decrease hemorrhage in vivo in a rabbit stroke model. Invest Radiol 2011; 46:202-207.
23. Zhao B Q, Suzuki Y, Kondo K, Ikeda Y, Umemura K. Combination of a free radical scavenger and heparin reduces cerebral hemorrhage after heparin treatment in a rabbit middle cerebral artery occlusion model. Stroke 2001; 32:2157-2163.
24. The European Agency for the Evaluation of Medicinal Products Human Medicines Evaluation Unit, Press release from the 40th Plenary Meeting of the Committee for Proprietary Medicinal Products. Available at: www.ema.europa.eu/docs/en_GB/document_library/Press_release/2009/12/WC500017427.pdf. Accessed Mar. 1, 2010.
25. The European Agency for the Evaluation of Medicinal Products Human Medicines Evaluation Unit, Withdrawal of the marketing authorization for the medicinal product EchoGen—dodecafluoropentane. Available at: www.ema.europa.eu/docs/en_GB/document_library/Public_statement/2009/12/WC500018334.pdf. Accessed Mar. 1, 2010.

Example 3. Dodecafluoropentane Emulsion Decreases Infarct Volume in a Rabbit Ischemic Stroke Model New Zealand White rabbits (n=40) were used. Animal procedures were as described in Example 2 above. Briefly, rabbits were sedated with intramuscular injection of ketamine, 30 mg/kg and xylazine, 3 mg/kg and anesthetized with isoflurane. A femoral artery was exposed, and a modified 65-cm angled-tip 3F catheter was used to select the ICA. Embolization of three 700-900 μm embolic spheres (Embosphere Microspheres; Biosphere Medical Inc.) flushed into the ICA occluded some branches, usually the middle cerebral artery (MCA) and anterior cerebral artery (ACA). To provide uniform deficits, rabbits with other occlusions were discarded.

Treatments were initiated according to group schedules using an ear vein catheter. Four hours following embolization, rabbits were euthanized with IV 1.5-mL of pentobarbital.

Rabbits were randomly assigned to 4 groups: 1) control, no therapy (n=7); 2) immediate DDFPe (n=8); 3) DDFPe at 30 minutes (n=6); 4) DDFPe at 60 minutes (n=7). Therapies were one dose of 2% w/v DDFPe IV, 0.6 mL/kg, at the designated group time and a second identical dose 90 minutes later.

Following euthanasia, the brain was harvested, immediately chilled in saline, and then sliced coronally at 0.4-cm intervals using a chilled brain mold. Brain sections (n=8) were placed in 1% 2,3,5-triphenyltetrazolium chloride for 45 minutes at 37° C., fixed in 10% formalin, and digitally photographed. Brain size and areas of infarction were measured using digital analysis (NIH ImageJ) in a blinded fashion. Percent infarct volume was calculated.

Because infarct volumes were not normally distributed, ranks of infarct volume were analyzed with PROC GLM of SAS (Kruskal-Wallis equivalent). Dunnett-adjusted p-values were used in comparing each DDFPe group to controls.
Results and Discussion Of 40 rabbits, angiography failed in 6, usually due to spasm, and 34 had successful angiography and embolization with occlusion of the MCA or ACA and exhibited infarcts (FIG. 9). Six also had occlusion of posterior cerebral or superior cerebellar arteries and were discarded, leaving 28 for analysis. Median percent infarct volumes were decreased (P=0.0054) for all rabbits treated with DDFPe (0.30%) compared with controls (3.20%). All individual group medians were lower than controls (2=0.20%, p=0.033; 3=0.35%, p=0.071; 4=0.30%, p=0.039) (FIG. 10).

Dodecafluoropentane (DDFPe) at body temperature transports many times more oxygen per weight volume than previous therapies using liquid fluorocarbon-based oxygen carriers such as liquid perfluorocarbons (PFC), which have largely failed to compensate for oxygen deficits. The simple IV dose of DDFPe is less than $\frac{1}{100}^{th}$ of other PFC based agents. The nano-sized droplets and bubbles pass, like tPA, through spaces smaller than red blood cells and transport oxygen to ischemic areas blocked from whole blood flow. Other PFC agents require larger doses and are retained within the body long-term. In human pharmacokinetic studies IV DDFPe is well tolerated, acts for about 2 hours, and is cleared by exhalation within hours.

This rabbit study shows clear benefit in decreased stroke volume compared with untreated controls, not only when given immediately, but also with delays of 30 or 60 minutes. While immediate administration could model preventive therapy in high-risk procedures, the delayed groups model usual strokes.

In addition to both ischemic and hemorrhagic acute strokes, clinical applications might also include pretreatment of high-risk cardiac and carotid surgeries or neurovascular or cardiac interventions providing a few hours of improved tissue oxygenation during iatrogenic ischemic episodes. Many strokes or myocardial infarctions caused by transient clot, bubbles, or hypoxia might be completely avoided. Both gaseous emboli and hypoperfusion episodes are transient phenomena and may require no additional therapy after DDFPe treatment.

Example 4. DDFPe Treatment 3 Hours after Embolization

Surgical procedures, angiographic treatments with DDFPe, measurement of infarctions and infarct volumes were as described in Example 2 above. Rabbits were randomly assigned to 6 groups: 1) control, no therapy; 2) immediate DDFPe; 3) DDFPe at 30 minutes; 4) DDFPe at 1 hr, 5) DDFPe at 2 hrs, and 6) DDFPe at 3 hrs.

Median percent infarct volumes were significantly decreased for all rabbits treated with DDFPe compared with controls, even 3 hrs after embolization (FIG. 11).

Example 5. Pretreatment with DDFPe and Treatment 7 Hours after Embolization

Surgical procedures, angiographic treatments with DDFPe, measurement of infarctions and infarct volumes were as described in Example 2 above. Rabbits were randomly assigned to 8 groups: 1) control, no therapy; 2) control, pretreated with DDFPe 7 hours before embolization, 3) immediate DDFPe; 4) DDFPe at 30 minutes; 5) DDFPe at 1 hr, 6) DDFPe at 2 hrs, 7) DDFPe at 3 hrs, and 8) DDFPe at 6 hrs.

Median percent infarct volumes were significantly decreased compared with controls for all rabbits treated with DDFPe up to 3 hrs after embolization (FIG. 12).

Example 6. Hyperacute and Acute DDFPe Treatment after Embolization

Surgical procedures, angiographic treatments with DDFPe, measurement of infarctions and infarct volumes were as described in Example 2 above. Rabbits were randomly assigned to 3 groups: 1) control, no therapy (7 rabbits); 2) a hyperacute treatment with DDFPe at 0 to 30 minutes after embolization, and 3) an acute treatment with DDFPe at 1 to 3 hours after embolization.

Median percent infarct volumes were significantly decreased compared with controls for all rabbits treated with DDFPe in the hyperacute and acute treatments with DDFPe (FIG. 13).

Example 7. Efficacy of DDFPe at 7 Hours is Maintained at Lower Doses and DDFPe Administration can Maintain Neuroprotection for 24 Hours without Revascularization Stroke is the fourth most common cause of death in the USA [1] and ischemic stroke affects 795,000 patients annually, costing $73.7 billion [2]. Few patients receive therapy and current best therapy improves outcomes to the point of independent lives in only 40% of those [3]. The treatment of ischemic stroke is currently focused on prompt revascularization and restoration of oxygenated blood flow. Due to time constraints and diagnostic requirements, therapy reaches fewer than 4% of patients and increases the urgency for the development of new therapies [2]. A neuroprotectant that extends the time window until safe thrombolytic or intra-arterial interventional therapy can be applied would have a profound impact, but no neuroprotectant has yet progressed successfully from animal models into human clinical therapy [4-6]. An effective oxygen transport substance may have therapeutic potential in diverse situations involving blood loss, hypoxia, and ischemic stroke, but this approach using other drugs including various liquid perfluorocarbons and other techniques has not yet proven clinically applicable.

Dodecafluoropentane is a perfluorocarbon (PFC) with a pentane base. In the current formulation, it exists as an emulsion (DDFPe) of nanodroplets, 250 to 300 nm in size when below 29° C. Although DDFP has a boiling point of 29° C., it apparently does not shift to microbubble form in the body at 37° C. due to intravascular pressure. Rather, the particle size expands only slightly allowing facilitation of respiratory gas dissolution. This mechanism transports high levels of oxygen and other gasses, much higher than other liquid phase PFCs with much higher boiling points [7]. The exceptionally small particle size may allow oxygen delivery into tissues unreachable by erythrocytes. This includes some flow even through occluded major blood vessels by transportation through flaws in clot, through collateral vessels, through microcirculation, and through diffusion gradients into hypoxic tissue. A previous study using a rabbit model of permanent embolic occlusion of the middle cerebral artery showed DDFPe decreased infarct volumes at 4 h when administration was delayed up to 3 h post stroke and therapy was successful for 7 h when begun 1 h following embolization [8, 9]. In this study, we assessed DDFPe dose response and efficacy in reducing infarct volume at 7 and 24 h post-embolization without lysis of arterial obstructions and also investigated basic blood pharmacokinetics.

Methods

All animal procedures were approved by the Institutional Animal Care and Use Committee.

DDFPe Effect on Infarct Volume.

These methods were described previously [8, 10]. New Zealand White rabbits (N=56; 5.1±0.10 kg) received cerebral angiography from a femoral artery approach. Embolic spheres (700-900 µm) were injected into the internal carotid artery occluding the middle cerebral and/or anterior cerebral arteries. Animals with other occlusions, 10% of cases, were discarded. In all treated groups, intravenous DDFPe (NuvOx Pharma, LLC, Tucson, Ariz.) dosing over 1-2 min with a 2% w/v emulsion began at 1 h post-embolization via a cannula placed in an ear vein and was repeated every 90 min until sacrifice. Rabbits were sacrificed at either 7 or 24 h post-embolization. At 7 h, the groups were: (1) control (embolized without treatment, N=6), or treatment with DDFPe: (2) 0.1 ml/kg (N=7), (3) 0.3 ml/kg (N=9), and (4) 0.6 ml/kg (N=8). At 24 h the groups were: (5) control (N=16), and treatment with DDFPe: (6) 0.1 ml/kg (N=10). Following euthanasia, the brain was harvested, immediately chilled in saline, and then sliced coronally at 4.0-mm intervals. Brain sections were placed in 1% 2,3,5-triphenyltetrazolium chloride (Sigma-Aldrich; St. Louis, Mo.) for 45 min at 37° C., fixed in 10% formalin, and digitally photographed (FIG. 14). Brain size and areas of infarction were measured using digital analysis (NIH ImageJ) by a technician blinded to treatment groups. Infarct volume was calculated as a percent of total brain volume.

Pharmacokinetic study. In alert New Zealand White rabbits (5.1±0.5 kg; N=8), cannulae were placed in a vein of one ear and in an artery of the other ear. After intravenous injection of DDFPe (0.6 ml/kg in a 2% w/v emulsion) arterial blood samples were taken over a period of 4 to 7 h. The dose of DDFPe was repeated every 90 min in four animals. Samples were stored at −20° C. until they were analyzed for DDFP content by a headspace gas chromatograph-mass spectrometer (Varian TSQ).

Statistics.

Because infarct volumes were not normally distributed, ranks of infarct volume were analyzed with PROC GLM of SAS software (Kruskal-Wallis equivalent). Blood levels of DDFP were analyzed for exponential curve fit and exponential decay time constant using KaleidaGraph software v4.01 (2005). Values are given as mean±standard error.

Results

Mean percent infarct volumes (% IV) decreased greatly for all DDFPe-treated groups compared with controls (Table 3, FIG. 14). For the 7 h study, the % IVs for the DDFPe groups were significantly different from the control group at p values less than 0.009, but were not different from each other. The average % IV for the 0.1, 0.3, and 0.6 ml/kg dose groups was 18.8% of the untreated control group. For the 24 h study using 0.1 ml/kg of DDFPe, the treated group was significantly different from the control group (p=0.03) and had an average % IV of 15.0% of control.

TABLE 3

Results of DDFPe treatment on stroke infarct volume at 7 or 24 h

| Group no. | DDFPe dosage | N | Sacrifice time (h) | P value (vs. control) |
|---|---|---|---|---|
| 1 | Control | 6 | 7 | — |
| 2 | 0.1 ml/kg | 7 | 7 | 0.004 |
| 3 | 0.3 ml/kg | 9 | 7 | 0.003 |
| 4 | 0.6 ml/kg | 8 | 7 | 0.009 |
| 5 | Control | 16 | 24 | — |
| 6 | 0.1 ml/kg | 20 | 24 | 0.03 |

DDFP blood levels were analyzed in animals receiving a single DDFPe dose of 0.6 ml/kg. Examination of the falling phase of blood levels of DDFP yielded peak levels of 1.97 to 3.34 µL/ml with a single exponential decay. The calculated mean half-life was 1.45±0.17 min. For curve fit, the mean R value for the N=4 animals was 0.958 (FIG. 15). Mean blood clearance was 78.5±24.9 ml/min/kg. Blood levels reached non-detectable levels within 30 min. Injections at 90 min intervals in four additional animals showed similar peaks and half-lives. After each dose of 0.6 ml/kg, blood levels returned to baseline and no sign of accumulation was seen with up to five doses.

DISCUSSION

Several perfluorocarbons have been extensively tested in the search for neuroprotectants and blood substitutes [11, 12]. Although animal studies have been very promising, no neuroprotectants have been successful in human trials [4-6]. The initial application of DDFPe as an ultrasound contrast agent was well tolerated in single doses in >2,000 humans for that purpose [9] before development stopped for economic reasons [13]. Only recently has the potential therapeutic aspect of this emulsion been investigated [8, 14, 15]. A preliminary study showed the potential as a neuroprotective agent with complete and permanent occlusion of cerebral arteries in rabbits and up to 3 h of delay in therapy. Over 80% of infarct volume was protected for up to 7 h [8] and duration was extended to 24 h in this study. In the present study, we tested decreasing doses of DDFPe for efficacy and described its basic pharmacokinetics.

Repeated doses show that protection can be maintained for a full 24 h using the smallest dose (0.1 ml/kg) every 90 min. The potential clinical applications are extremely broad and may change the basic paradigm for stroke, in both workup and therapy. A dose could be given in the field, provide a period of protection during transportation, be repeated at 90 min and provide a continuing period of protection during clinical workup in the hospital. This time advantage, a potential 3 h bonus with two injections in a most critical phase, could "pause the clock" on the "Time is Brain" concept at the time of first administration. Since expected good therapeutic results fall quickly with the passage of time, DDFPe as a neuroprotectant could dramatically increase the expected good outcomes of thrombolysis or thrombectomy. Two- or threefold improvement in infarct reduction may be possible for the patient who is finally ready to get therapy several hours after receiving DDFPe at 1 h. Multiple additional doses appear to further expand the "pause" and the limits are not yet defined. Bridging the first few hours following stroke onset may be the critical portion of therapy. If so, we speculate that it can possibly be a complete therapy if collateral flow can be recruited to supply the ischemic areas. Similar applications in cases of blood loss, hypoxia, or trauma may also be efficacious.

The small doses demonstrated here apparently avoid the toxicity of larger doses suggested in an animal study where pulmonary edema was encountered in dogs receiving rapid repeat intravenous injections [16]. Although single doses and double doses separated by 24 h appeared safe in over 2,000 human applications [13, 17], toxicity of more frequently administered repeated doses has not yet been defined. In addition, DDFPe can be damaged by uncontrolled fluctuations in storage conditions (i.e., hot/cold cycles) prior to use. This appears to enlarge droplet size. Use of this damaged form may have lead to pulmonary edema and severe toxicity in rabbits (unpublished data). The drug must be maintained at moderate room temperatures in storage but need not be refrigerated.

A mean half-life value of 1.45±0.17 min for DDFP in blood after a single 0.6 ml/kg dose agrees with a previous study in humans in which blood data showed a short half-life of 2.2±1.2 min [18]. The higher blood clearance rate of 78.5±24.9 ml/min/kg in rabbits compared to 30.1 to 48.6-ml/min/kg in humans may in part be due to the higher heart and respiratory rates and faster circulation time in rabbits. In the human study, 99% of DDFP in a single dose was recovered from expired air within 2 h [18]. This short half-life is not easily reconciled with the supportive effect of DDFPe lasting 90 to 120 min when similar doses were given for severe blood loss in swine [15] and rats [14]. Thus, the duration of effect of DDFPe greatly exceeds the duration of measurable blood levels. Analysis of levels of DDFP in rabbit organs is currently being done. One possibility is that DDFPe diffuses into organs and tissues at low levels. Thus, low levels of DDFPe would be available for time periods much longer than five half-lives as measured in blood. Another possibility is that molecules of DDFP assemble in series along blood vessels of the penumbra and pass along oxygen in a daisy-chain manner. The latter would require very low levels of DDFP. The effective level of DDFP would need to be rather low because in multiple dose studies in which DDFPe was given at 90 min intervals, the blood level of DDFP appeared to return to the baseline level less than 30 min after each dose.

Each dose tested in this study proved effective at reducing infarct volume. Alternative dose schedules or infusion schedules may be possible. The real limits on duration of effectiveness of a single dose will require additional study, although the previous swine studies showed continued effectiveness of between 90 and 120 min when given as an infusion over 30 min [14]. The lowest effective dose may be near or below the detection level for the analysis technique used.

Conclusion

Intravenous DDFPe protects brain from ischemic injury and significantly decreases infarct volumes in ischemic stroke. Although DDFPe has a short half-life in blood, 1.45±0.17 min, the effect of DDFPe is much longer, >90 min, which suggests the possibility of two or more compartments in the model.

REFERENCES

1. Kochanek K, Xu J, Murphy S L, Minino A M, Kung H-C(2011) Deaths: Final data for 2009. Natl Vital Stat Rep 60(3):1-117
2. Roger V L et al (2012) AHA statistical update: heart diseases and stroke statistics-2012 Update. Circulation 125:e2-e220, ePub Dec. 15, 2011
3. Saver J L, Jahan R, Levy El, Jovin T G, Baxter B, Nogueira R G, Clark W, Budzik R, Zaidat O O, Trialists SWIFT (2012) Solitaire flow restoration device versus the Merci Retriever in patients with acute ischemic stroke (SWIFT): a randomized, parallel-group, non-inferiority trial (2012). Lancet 380(9849):1241-1249
4. Donnan G A (2009) The 2007 Feinberg lecture: a new road map for neuroprotection. Stroke 39:242-248
5. Diener H C, Lees K R, Lyden P, Grotta J, Davalos A, Davis S M, Shuaib A, Ashwood T, Wasiewski W, Alderfer V, Hardemart H G, Rodichok L, SAINT I and II Investigators (2008) NXY-059 for the treatment of acute stroke: pooled analysis of the SAINT I and II Trials. Stroke 39:1751-1758
6. Heiss W D, Brainin M, Bornstein N M, Tuomilehto J, Hong Z, Cerebrolysin Acute Stroke Treatment in Asia (CASTA) Investigators (2012) Cerebrolysin in patients with acute ischemic stroke in Asia: result of a double-blind, placebo-controlled randomized trial. Stroke 43(3): 630-636
7. Johnson J L C, Dolezal M C, Kerschen A, Matsunaga T O, Unger E C (2009) In vitro comparison of dodecafluoropentane (DDFP), perfluorodecalin (PFD), and perfluoroctylbromide (PFOB) in the facilitation of oxygen exchange. Artif Cell Blood 37:156-162
8. Culp W C, Woods S D, Skinner R D, Brown A T, Lowery J D, Johnson J L H, Unger E C, Hennings L J, Borrelli M J, Roberson P K (2012) Dodecafluoropentane emulsion decreases infarct volume in a rabbit ischemic stroke model. J Vasc Intery Radiol 23:116-121
9. Correas J M, Quay S C (1996) EchoGen emulsion: a new ultrasound contrast agent based on phase shift colloids. Clin Radiol 51(S1):11-14
10. Culp W C, Woods S D, Brown A T, Lowery J D, Hennings L J, Skinner R D, Borrelli M J, Roberson P K. Three variations in rabbit angiographic stroke models. J Neurosci Meth, Epub ahead of print Nov. 8, 2012, doi: 10.1016/j/jneurometh.2012.10.107
11. Reiss J G (2005) Understanding the fundamentals of perfluorocarbons and perfluorocarbon emulsions relevant to in vivo oxygen delivery. Artif Cells Blood Substit Immobil Biotechnol 33:47-63
12. Remy B, Deby-Dupont G, Lamy M (1999) Red blood cell substitutes: fluorocarbon emulsions and haemoglobin solutions. Br Med Bull 55:277-298
13. The European Agency for the Evaluation of Medicinal Products Human Medicines Evaluation Unit, 27 Jul. 1998, CPMP/1342/98
14. Lundgren CEG, Bergoe G W, Tyssebotn I M (2006) Intravascular fluorocarbon-stabilized microbubbles protect against fatal anemia in rats. Artif Cell Blood Sub 34:473-486
15. Tyssebotn I M, Lundgren C E, Olszowka A J, Bergoe G W (2010) Hypoxia due to shunts in pig lung treated with 02 and fluorocarbon-derived intravascular microbubbles. Artif Cells Substit Immobil Biotechnol 38(2):79-89
16. Grayburn P A, Erickson J M, Excobar J, Womack L, Velasco C E (1995) Peripheral intravenous myocardial contrast echocardiography using a 2% dodecafluoropentane emulsion: identification of myocardial risk area and infarct size in the canine model of ischemia. J Am Coll Cardiol 26(5):1340-1347
17. Khor S P (2012) Amendment to the pharmacokinetic analysis of clinical data from study SON-3600-1004a: NuvOx Formal Study Report
18. Correas J M, Meuter A R, Singlas E, Kessler D R, Worah D, Quay S C (2001) Human pharmacokinetics of a perfluorocarbon ultrasound contrast agent evaluated with gas chromatography. Ultrasound Med Biol 27:565-570

Example 8. Combination DDFPe and tPA Therapy

In this example, a combination study was performed using aged clot with administration of 0.6 ml/kg IV DDFPe one hour after embolization, followed by standard IV tPA therapy for one hour. A second dose of IV DDFPe was given at 90 minutes. These animals survived to 24 hours. Controls (n=13) showed a mean infarct volume of 3.04% while the DDFPe animals, n=6, were 0.43%. These results show that the combination of DDFPe (limited to two doses for about 5 hours of coverage) and tPA therapy does produce improvement when occlusive clots are lysed and that no excessive bleeding occurs with reperfusion.

Example 9. Dodecafluoropentane Emulsion Decreases Infarct Volume and Neurological Deficit in a Rat Ischemic Stroke Model Introduction: Dodecafluoropentane emulsion (DDFPe), a perfluorocarbon approved for human use in Europe as an ultrasonographic contrast agent, has been shown in a rabbit permanent occlusion model of stroke to deliver oxygen as a nanodroplet to tissues suffering from ischemia, resulting in an 80% reduction in infarct volume compared to controls. We investigate the tissue-saving action of DDFPe in a second animal ischemic stroke model of permanent occlusion using Sprague Dawley (SD) rats and the effect of DDFPe on neurological outcomes.

Hypothesis: Intravenous DDFPe will reduce the percent brain infarct volume and neurological deficit in treatment animals compared to controls.

Methods: SD rats (n=26) underwent cauterization of the middle cerebral artery followed by ligation of the common carotid artery. Controls (n=11) received no treatment while treatment groups received either 1 (n=7) or 4 (n=8) doses of 2% w/v DDFPe at 0.6 mL/kg. The 1 dose group was injected 1 hour post-occlusion while the 4 dose group was additionally injected every 90 minutes until euthanasia. All animals underwent a neurological exam, and scores were assigned immediately before sacrifice at 6 hours post-occlusion. Brain tissue was treated with vital staining and percent infarct was measured.

Results: The mean±SE infarct volume percent for each group was 3.02%±0.74 for 1 dose, 1.70%±0.80 for 4 dose, and 8.76%±1.92 for control with percent infarct significantly reduced compared with controls (P=0.01 for 1 dose and P<0.01 for 4 dose). The 1 and 4 dose groups did not differ significantly in infarct volume (P=0.57). Mean neurological scores±SE were improved in the 4 dose treatments at 5.75±1.10 compared to controls (n=10) 9.20±1.17 (P=0.05). There was no significant difference between the 1 dose at 8.43±1.40 and control groups (P=0.68).

Conclusion: The current study demonstrates the ability of DDFPe to reduce infarct size and preserve neurological function. Considering the success of this and previous studies including prior safety profiles, it is clear that DDFPe should be moved to clinical stroke trials.

What is claimed is:

1. A method for reducing the infarct volume in a tissue of a human subject undergoing ischemia resulting from an ischemic event, the method comprising injecting intravenously into said subject, at a time ranging from immediately after the start of the ischemic event to 3 hours after the onset of symptoms, a perfluorocarbon emulsion comprising about 1% to about 5% w/v of dodecafluoropentane at a dosage of about 0.2 mg/kg to about 12 mg/kg of the subject, wherein the infarct volume is reduced by about 70% to about 90%.

2. The method of claim 1, wherein the subject is administered the perfluorocarbon emulsion in combination with an anticoagulant or thrombolytic agent.

3. The method of claim 2, wherein the subject is administered the perfluorocarbon emulsion in combination with tPA.

4. The method of claim 3, wherein the subject is further administered oxygen inhalation.

5. The method of claim 1, wherein the infarct volume is reduced without incidence of brain hemorrhage.

6. The method of claim 1, further comprising resolving the ischemic event.

7. The method of claim 1, wherein the ischemic event is stroke.

8. The method of claim 1, wherein the ischemic event is hypotension.

9. The method of claim 1, wherein injecting intravenously into said subject is performed as a bolus.

* * * * *